United States Patent
Paik et al.

(10) Patent No.: US 10,292,967 B2
(45) Date of Patent: May 21, 2019

(54) COMPOSITIONS COMPRISING CORNEOSCLERAL TISSUE CROSS-LINKING AGENTS

(71) Applicants: David Choohyun Paik, Cheltenham, PA (US); Stephen Lewis Trokel, New York, NY (US)

(72) Inventors: David Choohyun Paik, Cheltenham, PA (US); Stephen Lewis Trokel, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 16/133,260

(22) Filed: Sep. 17, 2018

(65) Prior Publication Data

US 2019/0015388 A1    Jan. 17, 2019

Related U.S. Application Data

(62) Division of application No. 15/125,558, filed as application No. PCT/US2015/020276 on Mar. 12, 2015, now Pat. No. 10,105,350.

(60) Provisional application No. 61/952,043, filed on Mar. 12, 2014, provisional application No. 62/088,383, filed on Dec. 5, 2014.

(51) Int. Cl.
| | |
|---|---|
| A61K 31/4166 | (2006.01) |
| A61K 33/00 | (2006.01) |
| A61K 31/4178 | (2006.01) |
| C07K 14/78 | (2006.01) |
| A61K 31/115 | (2006.01) |

(52) U.S. Cl.
CPC ........ *A61K 31/4166* (2013.01); *A61K 31/115* (2013.01); *A61K 31/4178* (2013.01); *A61K 33/00* (2013.01); *C07K 14/78* (2013.01)

(58) Field of Classification Search
CPC .............. A61K 31/4166; A61K 31/115; A61K 31/4178; A61K 33/00; C07K 14/78
USPC .......................................................... 514/389
See application file for complete search history.

(56) References Cited

U.S. PATENT DOCUMENTS

| | | |
|---|---|---|
| 5,459,073 A | 10/1995 | Ryan |
| 8,466,203 B2 | 6/2013 | Paik et al. |
| 2010/0173019 A1 | 7/2010 | Paik et al. |
| 2016/0374992 A1 | 12/2016 | Paik et al. |

OTHER PUBLICATIONS

International Search Report dated Jul. 8, 2015 in connection with PCT International Application No. PCT/US2015/020276.
International Preliminary Report on Patentability dated Sep. 13, 2016 in connection with PCT International Application No. PCT/US2015/020276.
Paik, DC et al. "Aliphatic β-Nitroalcohols for Therapeutic Corneoscleral Cross-Linking: Chemical Mechanisms and Higher Order Nitroalcohols", *Investigative Ophthalmology & Visual Science*, Feb. 2010, 51:2.
Li, X et al. "Mechanistic and Catalytic Studies of [Beta] β-Nitroalcohol Crosslinking with Polyamine", *Journal of Applied Polymer Science*, Jun. 15, 2013, 128(6).
Zeeman, R et al. "Crosslinking and Modification of Dermal Sheep Collagen Using 1,4-Butanediol Diglycidyl Ether" (1999).

*Primary Examiner* — Kristin A Vajda
(74) *Attorney, Agent, or Firm* — John P. White; Cooper & Dunham LLP

(57) ABSTRACT

A composition for opththalmic administration comprising a formaldehyde releasing agent, sodium bicarbonate, and an ophthalmically suitable carrier or excipient is provided.

12 Claims, 7 Drawing Sheets

Net apical displacement response over time for control and diazolidinyl urea cross-linked cornea at pH 8.5.

COMPOSITIONS COMPRISING CORNEOSCLERAL TISSUE CROSS-LINKING AGENTS

This application is a divisional of U.S. application Ser. No. 15/125,558, filed Sep. 12, 2016, now allowed, which is a § 371 national stage of PCT International Application No. PCT/US2015/020276, filed Mar. 12, 2015, and claims the benefit of U.S. Provisional Application No. 61/952,043; filed Mar. 12, 2014; and U.S. Provisional Application No. 62/088,383, filed Dec. 5, 2014, the contents of each of which are hereby incorporated by reference.

This invention was made with government support under grant EY020495 awarded by the National Institutes of Health. The Government has certain rights in this invention.

Throughout this application various publications are referenced. The disclosures of these documents in their entireties are hereby incorporated by reference into this application in order to more fully describe the state of the art to which this invention pertains.

BACKGROUND OF THE INVENTION

Collagen is a fundamental protein found in connective tissue in animals, and it is present in the cornea and sclera of the eye. Several eye disorders are related to defects in collagen structure and include keratoconus, keratectasia, progressive myopia, and possibly glaucoma.

Keratoconus is a debilitating, progressive eye disorder, which is believed to occur due to progressive slippage of collagen lamellae in the cornea, usually bilateral, beginning between ages 10 and 20. The cornea develops a conical shape, causing significant changes in the refractive power of the eye. While corrective lenses may help vision, corneal transplant surgery may be necessary if eyeglasses or contact lenses are inadequate. THE MERCK MANUAL OF DIAGNOSIS AND THERAPY 722 (Mark H. Beers and Robert Berkow eds., 17th ed. 1999).

Keratoconus is estimated to affect 1 person in about 435 to 2000 people in the general population. In its classical form, keratoconus commences at puberty and progresses into the third to fourth decade of life Rabinowitz, Y. S., "Keratoconus," *Surv. Opthal.* 1998; 43(4):297-319. Thus, its overall impact is magnified by virtue of the younger population that it afflicts. Clinically, the disease is marked by progressive thinning of the corneal stroma with resultant bulging and distortion of the thinned, weakened areas. This thinning and distortion is documented by optical and ultrasonic methods. The bulging, distorted cornea creates an optically imperfect surface to the eye that produces an increasingly irregular astigmatism and myopia. Contact lenses are used to correct these optical imperfections when spectacle lenses are no longer able to compensate for the induced optical distortion. When contact lens correction fails, only a corneal transplant will allow restoration of visual function. The need for corneal transplantation arises when the disease has progressed and central corneal scar formation occurs, or the distortion is so great that contact lenses can no longer be worn.

Although the underlying etiology of keratoconus remains unclear, there are two main mechanistic theories currently entertained. The first is related to destabilization of collagen lamellae through increased degradation via imbalances in endogenous proteases and/or their inhibitors. In this regard, the scientific evidence has been somewhat equivocal with some studies showing increased matrix-metalloproteinase activity and others reporting no change (reviewed by Collier, S. A., "Is the corneal degradation in keratoconus caused by matrix-metalloproteinases?" *Clin. Exp. Ophthalmol.* 2001; 29:340-344). An alternative theory regards collagen fibril slippage with no overall tissue loss. Meek, K. M., et al. have shown, using synchrotron X-ray scattering, that stromal lamellar organization is altered with an associated uneven distribution of collagen fibrillar mass. These changes are consistent with inter- and/or intra-lamellar slippage within the stromal layers of the keratoconic cornea, leading to central thinning. Meek, K. M., et al., "Changes in collagen orientation and distribution in keratoconus corneas," IOVS 2005; 46(6):1948-1956. The defect that would allow such slippage could be related to changes in the collagen to proteoglycan interactions and/or qualitative changes in the fibrillar collagens. Regarding this second point, very little is known about the qualitative biochemical collagen changes that occur in keratoconus. However, alterations in difunctional collagen cross-linking were reported decades ago. Cannon, J. and Foster, C. S., "Collagen crosslinking in keratoconus," IOVS 1978; 17(1):63-65; Oxlund, H. and Simonsen, A. H., "Biochemical studies of normal and keratoconus corneas," 1985; 63:666-669; Critchfield, J. W., et al., "Keratoconus: I, biochemical studies," *Exp. Eye Res.* 1988; 46:953-963. Regardless of the exact mechanism responsible for progressive corneal thinning, the pathologic changes that take place are accompanied by a loss of biomechanical strength. In this regard it has been shown that keratoconic corneas show a decreased stress for a given strain as compared to controls (i.e., decreased tissue stiffness) [Andreassen, T. T., et al., "Biomechanical properties of keratoconus and normal corneas," *Exp. Eye Res.* 1980; 31:435-441.] Andreassen, T. T., et al. also found that keratoconus collagen displayed a decreased resistance to enzymatic digestion with pepsin, a finding which is consistent with alterations in collagen cross-linking.

Current treatments for keratoconus either mask the surface irregularity with a variety of contact lenses, or attempt to improve the surface contour with intracorneal ring segments, lamellar keratoplasty, or excimer laser surgery. Binder, P. S., et al., "Keratoconus and corneal ectasia after LASIK," *J. Refract. Surg.* 2005; 21:749-752. However, the disease is progressive and none of these options obviates the need for eventual corneal transplantation.

Glaucoma is a group of disorders characterized by progressive damage to the eye at least partly due to increased intraocular pressure, the aqueous pressure in the eye. Increased intraocular pressure results from an inadequate aqueous outflow from the eye due to an obstruction in the trabecular meshwork from which the eye drains. Collagen is necessary to maintain the structural integrity of the trabecular meshwork. Rehnberg, M., et al., "Collagen distribution in the lamina cribosa and the trabecular meshwork of the human eye." *Brit. J. Opthalmol.* 71:886-92 (1987). Open-angle glaucoma can be treated with medical, laser, or surgical therapy to prevent damage to the optic nerve and visual field by stabilizing the intraocular pressure. THE MERCK MANUAL OF DIAGNOSIS AND THERAPY 733-36 (Mark H. Beers and Robert Berkow eds., 17th ed. 1999).

In myopia, or nearsightedness, the image of a distant object is focused in front of the retina because the axis of the eyeball is too long or the refractory power of the eye is too strong. Rays of light fall in front of the retina because the cornea is too steep or the axial length of the eye is too long. Without glasses, distant images are blurry, but near objects can be seen clearly. While glasses or contact lenses correct vision, refractive surgery decreases a patient's dependence on glasses or contact lenses. Progressive myopia is a condition associated with high refractive error and subnormal visual acuity after correction. This form of myopia gets progressively worse over time. THE MERCK MANUAL OF DIAGNOSIS AND THERAPY 741-43 (Mark H. Beers and Robert Berkow eds., 17th ed. 1999). The development of severe myopia is associated with scleral thinning and changes in the diameter of scleral collagen fibrils in humans. McBrien, N. A., et al., "Structural and Ultrastructural Changes to the Sclera in a Mammalian Model of High Myopia." *Investigative Ophthalmol. & Visual Sci.* 42:2179-87 (2001).

Refractive surgery alters the curvature of the cornea to allow light rays to come to focus closer to the retina, thus improving uncorrected vision. In myopia, the central corneal curvature is flattened. However, ideal candidates for refractive surgery are people with healthy eyes who are not satisfied wearing glasses or contact lenses for their daily or recreational activities. Candidates for refractive surgery should not have a history of collagen vascular disease because of potential problems with wound healing. As keratoconus is a progressive thinning of the cornea, thinning the cornea further with refractive surgery may contribute to the advancement of the disease. Huang, X., et al., "Research of corneal ectasia following laser in-situ keratomileusis in rabbits." *Yan Ke Xue Bao*, 18(2):119-22 (2002). The side effects of refractive surgery include temporary foreign-body sensation, glare, and halos. Potential complications include over- and undercorrection, infection, irregular astigmatism, and, in excimer laser procedures, haze formation. Permanent changes in the central cornea caused by infection, irregular astigmatism, or haze formation could result in a loss of best corrected acuity.

Keratectasia is the protrusion of a thinned, scarred cornea. In laser in situ keratomileusis (LASIK), if the laser removes too much tissue, or the flap is made too deep, the cornea can become weak and distorted, leading to keratectasia. LASIK is contraindicated for patients with thin corneas, or those with keratectasia as a result of a prior LASIK procedure. Rigid gas permeable contact lenses are the recommended treatment for correcting vision in these patients. Kim, H., et al., "Keratectasia after Laser in situ Keratomileusis." *Intl. J. Ophthalmol.* 220:58-64 (2006).

A major breakthrough in the treatment of keratoconus and related keratectasias has been realized. Recent work by the German group of Wollensak, Spoerl, and Seiler has shown that cross-linking corneal collagen through application of riboflavin and ultraviolet light (UVR) can limit progressive vision loss in keratoconus patients. This modality represents a method through which stabilization of the corneal collagen lamellae and has been shown to prevent the progressive thinning of the cornea and loss of vision observed in keratoconus patients. This treatment involves the serial applications of riboflavin (0.1%) onto a de-epithelialized human cornea followed by exposure of the riboflavin saturated tissue to ultraviolet radiation in a UVA-370 nanometer wavelength region, at 3 mW/cm$^2$ radiant energy. The patient is treated with antibiotic drops to prevent infection and oral pain medicine after the procedure. Literature accruing over the past 9 years has described the utility of photochemical cross-linking using UVA irradiation ($\lambda$max=370 nm) with riboflavin as a photosensitizer (UVR). The work of the German group of Wollensak, G., Spoerl, E., and Seiler T., has shown that this method of cross-linking the collagen within the corneal stroma has proven effective in limiting the progression of corneal thinning, distortion, and resulting optical degradation of the eye. Wollensak, G., et al., "Riboflavin/ultraviolet-A-induced collagen crosslinking for the treatment of keratoconus." *Am. J. Ophthalmol.* 2003; 135: 620-27. Despite these successes, the UVR therapy poses attendant risks, particularly related to ultraviolet irradiation. As such, this therapy has yet to gain FDA approval in the US.

Because riboflavin tissue penetration is limited by the corneal epithelium, it is necessary to remove the corneal epithelium by scraping prior to riboflavin application. Removal of the corneal epithelium exposes the cornea to a risk of infection and causes significant pain. In addition, keratocyte (Wollensak, G., et al., "T. keratocyte cytotoxicity of riboflavin/UVA treatment in vitro." *Eye*, 18:718-22 (2004); Wollensak, G., et al., "Keratocyte apoptosis after corneal collagen cross-linking using riboflavin/UVA treatment." *Cornea*, 23(1):43-49 (2004)) and corneal endothelial cell toxicity (Wollensak, G., et al., "Corneal endothelial cytotoxicity of riboflavin/UVA treatment in vitro." *Ophthalmic Res.*, 35:324-28 (2003)) can occur with application of riboflavin/UVA to the cornea. In a similar manner, application of this therapy to the posterior sclera has been reported to damage cells in the photoreceptor, outer nuclear, and retinal pigment epithelial layers (Wollensak, G., et al., "Cross-linking of scleral collagen in the rabbit using riboflavin and UVA." *Acta Ophthalmologica Scandinavica*, 83:477-82 (2005).

Clinical trials in Europe (Caporossi, A., et al., "Parasurgical therapy for keratoconus by riboflavin-ultraviolet type A rays induced cross-linking of corneal collagen: Preliminary refractive results in an Italian study," *J. Cataract Refract. Surg.* 2006; 32:837-845; Wollensak, G., "Crosslinking treatment of progressive keratoconus: new hope," *Cur. Opin. Ophthal.* 2006; 17:356-360) have generated significant interest in initiating clinical trials in the United States. The early reports from this therapy were encouraging. After 5 years in the Dresden study, individuals who underwent this treatment protocol did not yet show progression of their keratoconus. Based on these encouraging results, corneal cross-linking therapy has been extended to include patients with related disorders such as the ectasia that occurs following LASIK (Laser-Assisted In situ Keratomileusis) and PRK (Photorefractive Keratectomy) excimer refractive surgery (Binder, P. S., et al., 2005). These are devastating complications of keratorefractive surgery in today's clinical practice. Anecdotal reports have also emerged reporting the use of collagen cross-linking as an effective means to control difficult-to-treat corneal fungal infections and corneal melts.

Despite these successes, the UVR therapy poses attendant risks, particularly related to ultraviolet irradiation. As such, this therapy has encountered difficulty gaining FDA approval and is currently unavailable in the United States. Because free oxygen radical formation occurs with riboflavin photolysis (Baier, J., et al., "Singlet oxygen generation by UVA light exposure of endogenous photosensitizers," *Biophys. J.* 2006; 91:1452-1459), this cross-linking method has a negative impact on cell viability. Indeed, keratocyte (Wollensak, G., et al., 2004) and corneal endothelial cell toxicity (Wollensak, G., et al., 2003) does occur with application of this therapy to the cornea. As a result of such toxicity, it has been recommended that patients with particularly thin central corneas (<400 µm) not undergo this therapy since the depth of UVA penetration exposes the endothelial cells (which are vital to maintaining corneal clarity through water regulation) to toxic photochemical damage. Furthermore, the long-term risks of this photochemical exposure are not known. Secondly, deep tissue penetration by the riboflavin requires removal of the corneal epithelium, a procedure that increases morbidity and complications. This requires analgesics and antibiotics following the UVR cross-linking procedure.

More recently, a topical self-administered compound has been suggested for producing a comparable degree of collagen cross-linking to UVR therapy, as described in U.S. Pat. No. 8,466,203. U.S. Pat. No. 8,466,203 describes a method of cross-linking collagen in a subject's collagenous tissue by contacting the collagenous tissue with an amount of a nitrogen oxide-containing compound, such as a nitroalcohol, to cross-link the collagen in the collagenous tissue.

Thus, the growing clinical success of UVA-riboflavin photochemical corneal cross-linking (CXL) to halt the progression of keratoconus (KC) and post-LASIK keratectasia suggests that increasing mechanical tissue strength in vivo can be beneficial. UVA-riboflavin mediated photochemical cross-linking (CXL) increases the stiffness of corneal tissue as shown in animal studies using post-mortem mechanical strip testing. Spoerl et al., *Exp Eye Res* 66:97-103 (1998). A majority of patients ultimately gain improvements in topography and gain lines of vision. Raiskup-Wolf et al., *J Cataract Refract Surg* 34:796-801 (2008). Application of CXL has been extended to treat corneal edema, corneal melting, and corneal infections.

As clinical trials involving CXL progress in the United States, suggestions have been made to extend its use to the sclera as a treatment for progressive myopia (Wollensak et al., *J Cataract Refract Surg* 30:689-695 (2004)), since biomechanical weakening occurs during progressive globe elongation. Scleral cross-linking with UVA-riboflavin technology has been reported but may be difficult to carry out in the posterior region of the sclera without the use of surgical means. Also, of concern is the potential of damaging the neural retina during UVA irradiation. The use of injectable pharmacologic agents that could cross-link the sclera as an alternative to photochemical activation is being explored and include glyceraldehyde, glutaraldehyde, genipin, and nitroalcohols. Hoang et al., IOVS 54:ARVO E-Abstract 5169 (2013).

The present disclosure serves as an extension of previous work using nitroalcohols, where the corneal and scleral cross-linking efficacy of several related though potentially more potent chemicals from a group known as formaldehyde releasing agents (FARs) was tested. These compounds are used as preservatives in a wide array of popular cosmetic and personal care products, such as skin care products, body wash, fingernail polish and shampoo, including the former formula for Johnson & Johnson's "No More Tears" Baby Shampoo. FARs have also been employed in the textile industry as cross-linking agents to impart anti-wrinkle properties to clothing. Considering their use in everyday items that come into direct contact with the human body, examination of the efficacy and cell toxicity of FARs as tissue cross-linking agents was a first step in their potential development for clinical use.

SUMMARY OF THE INVENTION

This invention provides a method of cross-linking collagen present in a collagenous tissue comprising contacting the collagenous tissue with an amount of a formaldehyde releasing agent effective to cross-link the collagen.

This invention also provides a method of inhibiting loss of structural integrity of a collagenous tissue during transplantation-related transport comprising contacting the collagenous tissue with an amount of a formaldehyde releasing agent effective to inhibit loss of structural integrity of the collagenous tissue.

This invention also provides a composition for ophthalmic administration comprising a formaldehyde releasing agent, sodium bicarbonate, and ophthalmically suitable carriers or excipients.

Finally, this invention provides a method of altering the refractive power of a cornea comprising contacting the cornea with a formaldehyde releasing agent so as to effect cross-linking in the cornea and thereby alter the refractive power of the cornea.

DETAILED DESCRIPTION OF THE INVENTION

Figure 1:
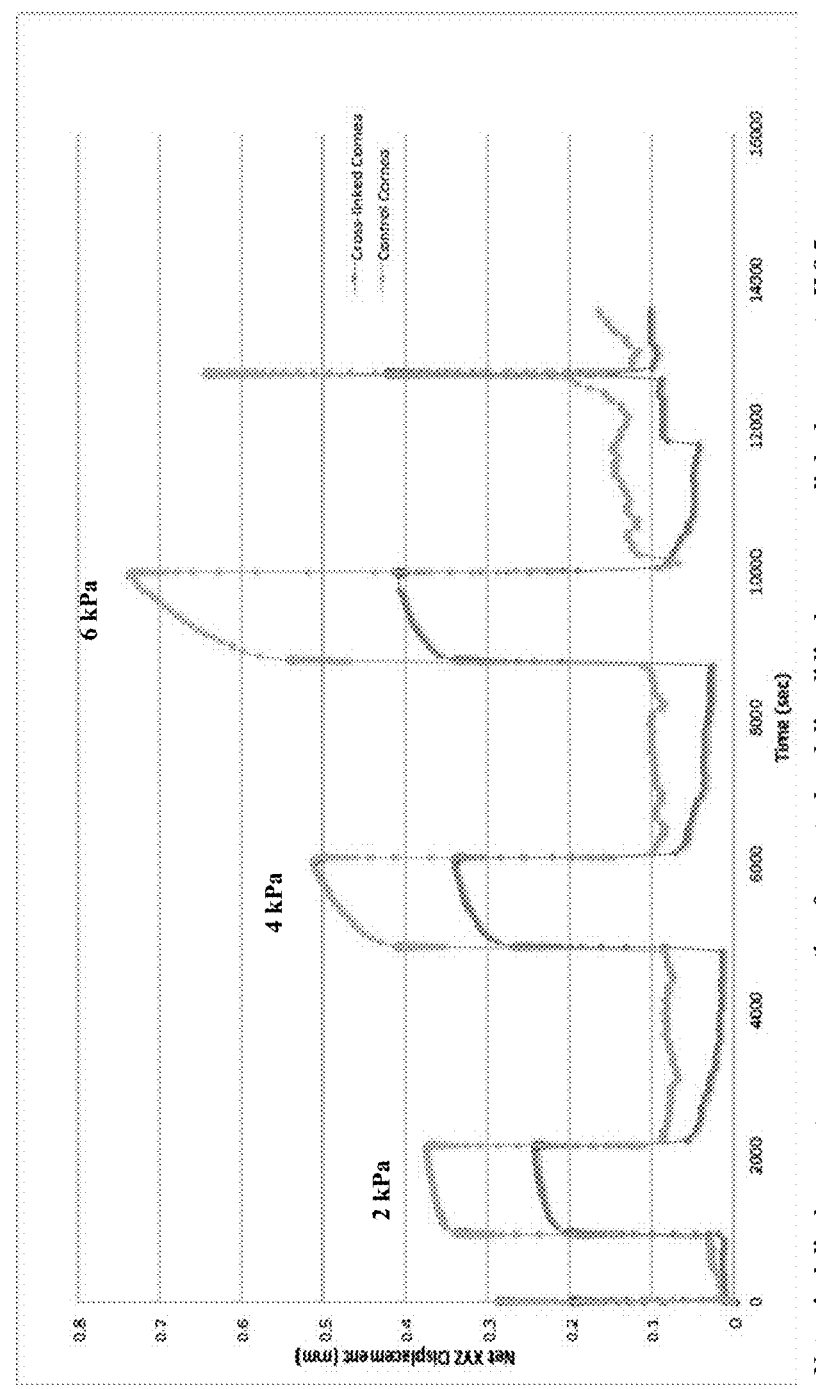
FIG. 1—Net apical displacement over time for a control cornea and a cornea cross-linked with N-hydroxymethyl-N-(1,3-di(hydroxymethyl)-2,5-dioxoimidazolidin-4-yl)-N'-hydroxy-methylurea (diazolidinyl urea) at pH 8.5.

This invention provides a method of cross-linking collagen present in a collagenous tissue comprising contacting the collagenous tissue with an amount of a formaldehyde releasing agent effective to cross-link the collagen. In one embodiment, the collagenous tissue is cornea, sclera, skin, tendon, fascia, bone, or cartilage. In one embodiment, the collagenous tissue is cornea, and the cornea is human cornea.

In one embodiment of the invention, the collagenous tissue is present in a subject. In a preferred embodiment, the collagenous tissue is cornea and the subject is afflicted with keratoconus or keratectasia.

In one embodiment, the formaldehyde releasing agent is present in a solution. In another embodiment, the formaldehyde releasing agent is in an aqueous solution having a pH effective for cross-linking. In a specific embodiment, the aqueous solution has a pH value of 7.4. In another specific embodiment, the aqueous solution has a pH value of 8.5. In one embodiment, the formaldehyde releasing agent is present in an aqueous solution comprising sodium bicarbonate.

In various embodiments, the contacting of the formaldehyde releasing agent to the collagenous tissue is performed by intermittent administration of the formaldehyde releasing agent to the collagenous tissue for a duration of time effective to cross-link collagen. In various embodiments, the solution is administered at intervals of one to ten times per day over a period of one day to one hundred and eighty days. In a specific embodiment, the solution is administered one to four times per day over a period of forty-two days. By administered one to ten times per day, it is meant that all integer unit amounts within the range are specifically disclosed as part of the invention. Thus, 2, 3, . . . 8, 9 administrations are included as embodiments of this invention. Similarly, the administration may be over a period of 2 days, 3 days . . . 178 days, or 179 days, and each integer value of days is included as an embodiment of this invention.

In one embodiment of this invention, the solution is administered as a composition selected from the group consisting of ophthalmic drops, ophthalmic salve, ophthalmic ointment, ophthalmic spray, subconjunctival injection, or intravitreal injection, contact lens, conjunctival insert, ocular time release insert, and sustained release implant. In a preferred embodiment, the solution is administered as an ophthalmic drop.

This invention also provides a method of inhibiting loss of structural integrity of a collagenous tissue during transplantation-related transport comprising contacting the collagenous tissue with an amount of a formaldehyde releasing agent effective to inhibit loss of structural integrity of the collagenous tissue. In one embodiment, the collagenous tissue is contacted with the formaldehyde releasing agent before removal of the collagenous tissue from the donor subject. In another embodiment, the collagenous tissue is incubated during transport from the transplant donor. In a specific embodiment, the transplant donor is a human. In one embodiment, the collagenous tissue is a heart valve. In another embodiment, the collagenous tissue is skin. In another embodiment, the collagenous tissue is cornea. In another embodiment, the collagenous tissue is sclera. In another embodiment, the collagenous tissue is tendon. In another embodiment, the collagenous tissue is fascia. In another embodiment, the collagenous tissue is bone. In another embodiment, the collagenous tissue is cartilage. In one embodiment, the collagenous tissue is human tissue.

In one embodiment, the contacting is at a temperature effective to inhibit loss of structural integrity of the collagenous tissue. In a specific embodiment, the temperature is greater than 60° C. In another specific embodiment, the temperature is greater than 62° C.

This invention also provides a composition for ophthalmic administration comprising a formaldehyde releasing agent, sodium bicarbonate, and ophthalmically suitable carriers or excipients.

In one embodiment, the formaldehyde releasing agent is in an aqueous solution having a pH effective for cross-linking. In a specific embodiment, the aqueous solution has a pH value of 7.4. In another specific embodiment, the aqueous solution has a pH value of 8.5.

This invention also provides a method of altering the refractive power of a cornea comprising contacting the cornea with a formaldehyde releasing agent so as to effect cross-linking in the cornea and thereby alter the refractive power of the cornea. In one embodiment, the refractive power of the cornea is increased. In another embodiment, the cross-linking effected in the cornea causes a surface contour of the cornea to change shape. In another embodiment, the cornea is an isolated cornea. In another embodiment, the cornea is human cornea.

In various embodiments, the formaldehyde releasing agent is 1-(phenylmethoxy)-methanol, N-hydroxymethyl-N-(1,3-di(hydroxymethyl)-2,5-dioxoimidazolidin-4-yl)-W-hydroxy-methylurea, 1,3-dimethylol-5,5-dimethyl-hydantoin, N,N'-methylenebis[N-[3-(hydroxymethyl)-2,5-dioxo-4-imidazolidinyl]]-urea, sodium hydroxymethyl glycinate, 5-bromo-5-nitro-1,3-dioxane, 2-bromo-2-nitropropane-1,3-diol, 3,5,7-triaza-1-azoniatricyclo[3.3.1.13,7]decane,1-(3-chloro-2-propen-1-yl)-chloride(1:1), 4,5-dihydroxy-1,3-dimethyl-2-Imidazolidinone, 4,5-dihydroxy-1,3-bis(hydroxymethyl)-2-Imidazolidinone, tetrahydro-1,3-bis(hydroxymethyl)-2(1H)-pyrimidinone, tetrahydro-1,3,4,6-tetrakis(hydroxymethyl)-imidazo[4,5-d]imidazole-2,5(1H,3H)-dione, polyoxymethylene urea, 4,4-dimethyloxazolidine, 7a-ethyldihydro-1H,3H,5H-oxazolo[3,4-c]oxazole, 4,5-dihydroxy-1,3-bis(hydroxymethyl)-2-imidazolidinone methylated, dimethylhydantoin formaldehyde resin, 4,5-dihydroxy-1,3-bis(hydroxymethyl)-2-imidazolidinone, 1,3-bis(hydroxymethyl)-2-imidazolidinone, N,N'-bis(hydroxymethyl)-urea, 1,3-ethyleneurea, (Z)-3-(bis(2-hydroxyethyl)amino)-2-(2-hydroxyethyl(hydroxymethyl)amino) prop-2-en-1-ol, 1,3,5-trietethyl-1,3,5-tiazinane, 4,5-dihydroxy-2-imidazolidinone, 1-(hydroxymethyl)-5,5-dimethyl-2,4-Imidazolidinedione, 1,3,5,7-tetraazatricyclo[3.3.1.13,7]decane, 4,4'-methylenebis-morpholine, 2-chloro-N-(hydroxymethyl)-acetamide, N-(hydroxymethyl)-urea, polyoxymethylene melamine, 1,1'-[methylenebis(oxymethylene)]bis-benzene, 1,6-dihydroxy-2-5-dioxahexane (1,1'-[1,2-ethanediylbis(oxy)]bis-methanol, 2,4-imidazolidinedione, hydroxymethyl-5-5-dimethyl-2-4-imidazolidinedione, 3-hydroxymethyl-5-5-dimethylimidazolidine-2,4-dione, dimethoxy-methane, N-methylolethanolamine, 1H,3H,5H-oxazolo[3,4-c]oxazole-7a(7H)-methanol, Bioban N-95 (mixture of 5-methyl-1-aza-3,7-dioxabicyclo[3.3.0]octane, 5-hydroxymethoxymethyl-1-aZa-3,7-dioxabicyclo[3.3.0]octane, and higher hydroxyalkoxymethyl oligomers), 5-methyl-1-aza-3,7-dioxabicyclo[3.3.0]octane, 4,4-dimethyl-oxazolidine, 4-ethyl-2-(1-methylethyl)-oxazolidine, 2-(hydroxymethyl)-2-nitro-1,3-propanediol, diethylamine/2-methyl-2 nitro-1,3-propanediol, dimethylamine-2-methyl-2-nitro-1,3-propanediol, pyrrolidine/2-methyl 2-nitro-1,3-propanediol, 2-furfural/2-methyl 2-nitro-1,3-propanol, N-hydroxy-2-propanamine, N-hydroxy-1-propanamine, N-hydroxy-ethanamine, N-hydroxy-2-methyl-2-propanamine, N-hydroxy-cyclohexanamine, N-ethyl-N-hydroxy-ethanamine, 1,1'-[methylenebis(oxy)]bis[2-methyl-2-nitro-(9CI)]-propane, hydroxylamine (HA) nitrone, N-ethylhydroxylamine (EHA) nitrone, N-propylhydroxylamine (PHA) nitrone, N-t-butyl hydroxylamine (tBuHA) nitrone, Cyclohexanedicarboxaldehyde (CHDA)-bis-isopropylhydroxylamine (IPHA) nitrone, N-benzyl hydroxylamine (N-BzHA) nitrone, or vanillin-isopropylhydroxylamine (IPHA) nitrone. In a preferred embodiment, the formaldehyde releasing agent is 1-(phenylmethoxy)-methanol, N-hydroxymethyl-N-(1,3-di(hydroxymethyl)-2,5-dioxoimidazolidin-4-yl)-N'-hydroxy-methylurea, 1,3-dimethylol-5,5-dimethyl-hydantoin, N,N'-methylenebis[N-[3-(hydroxymethyl)-2,5-dioxo-4-imidazolidinyl]]-urea, sodium hydroxymethyl glycinate, or 5-methyl-1-aza-3,7-dioxabicyclo[3.3.0]octane. In a more preferred embodiment, the formaldehyde releasing agent is N-hydroxymethyl-N-(1,3-di(hydroxymethyl)-2,5-dioxoimidazolidin-4-yl)-N'-hydroxy-methylurea.

As used herein, "collagenous tissue" refers to any bodily tissue that contains the protein collagen, such as skin, blood vessels, heart valve, tendons, fascia, bone, cartilage, tendonous tissue, and eye tissues such as the cornea, sclera, and retina.

As used herein, "corneoscleral disorder" is any disease, condition, or abnormality of the cornea and/or scleral tissue of the eye involving a loss of stiffness and/or contour changes of the eye. Thus, the corneoscleral disorder may be keratoconus, keratectasia, progressive myopia, or glaucoma.

As used herein, "formaldehyde releasing agent" or "formaldehyde releaser" (FAR) is a compound, often used as a preservative in cosmetics, which is able to release formaldehyde, such as benzyl hemiformal (1-(phenylmethoxy)-methanol), diazolidinyl urea (N-hydroxymethyl-N-(1,3-di(hydroxymethyl)-2,5-dioxoimidazolidin-4-yl)-N'-hydroxymethylurea), DMDM hydantoin (1,3-dimethylol-5,5-dimethyl-hydantoin), imidazolidinyl urea (N,N'-methylenebis[N-[3-(hydroxymethyl)-2,5-dioxo-4-imidazolidinyl]]-urea), sodium hydroxymethyl glycinate, 5-bromo-5-nitro-1,3-dioxane, bronopol (2-bromo-2-nitropropane-1,3-Diol), quaternium-15 (3,5,7-triaza-1-azoniatricyclo[3.3.1.13,7]decane,1-(3-chloro-2-propen-1-yl)-chloride (1:1)), 1,3-dimethyl-4,5-dihydroxyethyleneurea (4,5-dihydroxy-1,3-dimethyl-2-Imidazolidinone), dimethylol dihydroxyethyleneurea (4,5-dihydroxy-1,3-bis(hydroxymethyl)-2-imidazolidinone), dimethylol propyleneurea (tetrahydro-1,3-bis(hydroxymethyl)-2(1H)-pyrimidinone), tetramethylol acetylenediurea (tetrahydro-1,3,4,6-tetrakis(hydroxymethyl)-imidazo[4,5-d]imidazole-2,5(1H,3H)-dione), polyoxymethylene urea (urea polymer with formaldehyde), 4,4-dimethylyoxazolidine (3,4,4-trimethyloxazolidine with 4,4-dimethyloxazolidine), 7a-ethyldihydro-1H,3H,5H-oxazolo[3,4-c]oxazole, dihydroxy-dimethylol-ethylene urea methylated (4,5-dihydroxy-1,3-bis(hydroxymethyl)-2-imidazolidinone methylated), dimethylhydantoin formaldehyde resin (formaldehyde, polymer with 5,5-dimethyl-2,4-imidazolidinedione, dimethylhydroxyethyleneurea (4,5-dihydroxy-1,3-bis(hydroxymethyl)-2-imidazolidinone), dimethylolethyleneurea (1,3-bis(hydroxymethyl)-2-imidazolidinone), dimethylol urea (N,N'-bis(hydroxymethyl)-urea), 2-imidazolidinone (1,3-ethyleneurea), (Z)-3-(bis(2-hydroxyethyl)amino)-2-(2-hydroxyethyl-(hydroxymethyl)amino) prop-2-en-1-ol, 1,3,5-trietethyl-1,3,5-tiazinane, glyoxalurea (4,5-dihydroxy-2-imidazolidinone), MDM hydantoin (1-(hydroxymethyl)-5,5-dimethyl-2,4-imidazolidinedione), methenamine (1,3,5,7-tetraazatricyclo[3.3.1.13,7]decane), N,N'-methylenebismorpholine (4,4'-methylenebis-morpholine), 2-chloro-N-(hydroxymethyl)-acetamide, methylol urea (N-(hydroxymethyl)-urea), polyoxymethylene melamine (urea, polymer with formaldehyde and 1,3,5-triazine-2,4,6-triamine), phenylmethoxymehoxymethylbenzene (1,1'-[methylenebis(oxymethylene)]bis-benzene), 1,6-dihydroxy-2-5-dioxahexane (1,1'-[1,2-ethanediylbis(oxy)]bis-methanol), hydantoin (2,4-imidazolidinedione), hydroxymethyl-5-5-dimethyl-2-4-imidazolidinedione, 3-hydroxymethyl-5-5-dimethylimidazolidine-2,4-dione, methylol (dimethoxy-methane), N-methylolethanolamine (2-(hydroxymethylamino) ethanol), 1H,3H,5H-oxazolo[3,4-c]oxazole-7a(7H)-methanol, Bioban N-95 (mixture of 5-methyl-1-aza-3,7-dioxabicyclo[3.3.0]octane, 5-hydroxymethoxymethyl-1-aZa-3,7-dioxabicyclo[3.3.0]octane, and higher hydroxyalkoxymethyl oligomers), 5-methyl-1-aza-3,7-dioxabicyclo[3.3.0]octane, 4,4-dimethyl-oxazolidine, 4-ethyl-2-(1-methylethyl)-oxazolidine, 2-(hydroxymethyl)-2-nitro-1,3-propanediol, diethylamine/2-methyl-2 nitro-1,3-propanediol, dimethylamine-2-methyl-2-nitro-1,3-propanediol, pyrrolidine/2-methyl-2-nitro 1,3-propanediol, 2-furfural/2-methyl 2-nitro-1,3-propanol, N-hydroxy-2-propanamine, N-hydroxy-1-propanamine, N-hydroxy-ethanamine, N-hydroxy-2-methyl-2-propanamine, N-hydroxy-cyclohexanamine, N-ethyl-N-hydroxy-ethanamine, 1,1'-[methylenebis(oxy)]bis[2-methyl-2-nitro-(9CI)]-propane, hydroxylamine (HA) nitrone, N-ethylhydroxylamine (ERA) nitrone, N-propylhydroxylamine (PHA) nitrone, N-t-butyl hydroxylamine (tBuHA) nitrone, cyclohexanedicarboxaldehyde (CHDA)-bis-isopropylhydroxylamine (IPHA) nitrone, N-benzyl hydroxylamine (N-BzHA) nitrone, and vanillin-Isopropylhydroxylamine (IPHA) nitrone.

The formaldehyde releasing agent can be administered in admixture with ophthalmically suitable excipients or carriers suitably selected with respect to the intended form of administration and as consistent with conventional ophthalmical practices.

It is to be understood that the invention is not limited in its application to the details set forth in the description or as exemplified. The invention encompasses other embodiments and is capable of being practiced or carried out in various ways. Also, it is to be understood that the phraseology and terminology employed herein is for the purpose of description and should not be regarded as limiting.

EXAMPLES

First Experimental Details
Cross-Linking Using Formaldehyde Releasing Agents (FARs)

A listing of formaldehyde releasing agents (FARs) was gathered from literature review. Sixty-four (64) formaldehyde releasing agents, regularly found in cosmetics, were identified from the literature. Each formaldehyde releasing agent was analyzed with respect to relevant characteristics for cross-linking, such as molecular weight, carcinogenicity/mutagenicity, toxicity, hydrophobicity, and commercial availability.

Based on this analysis, formaldehyde releasing agents were selected for efficacy screening using an ex vivo rabbit corneal cross-linking simulation setup, as described below.

0.5% proparacaine was applied prior to the cross-linking solution. A cross-linking solution containing the formaldehyde releasing agent was then administered via a corneal reservoir for 30 minutes in 0.1M $NaHCO_3$ at either pH 7.4 or 8.5. The epithelium was left intact. The control contralateral eye was treated identically with vehicle.

Effectiveness of cross-linking was based on shifts in thermal denaturation temperature (Tm) as measured by differential scanning calorimetry (DSC) (Perkin-Elmer DSC 6000). Favorable DSC results were validated using biomechanical inflation tests with digital image correlation (DIC) as previously described by Myers et al.

Second Experimental Details
Chemical Registry

A chemical registry of formaldehyde releasers (FARs) commonly found in cosmetics and other personal care products (PCPs) was compiled from a review of the literature. Information used to assemble this registry included characteristics relevant to tissue cross-linking such as molecular weight, European Union maximum allowed concentration (i.e. "max allowed"), carcinogenicity/mutagenicity, toxicity, hydrophobicity (log P), efficacy of formaldehyde release, and commercial availability of the chemicals. From the FARs identified, five compounds with favorable profiles were selected for cross-linking efficacy and toxicity evaluation. These compounds include diazolidinyl urea (DAU), imidazolidinyl urea (IMU), DMDM hydantoin (DMDM), sodium hydroxymethylglycinate (SMG), and 5-Ethyl-3,7-dioxa-1-azabicyclo [3.3.0] octane (OCT), which were specifically chosen because of the vastness of their use in cosmetics and PCPs as well as on their ability to donate formaldehyde in solution under equilibrium conditions. The cross-linking efficacy and toxicity of two additional FARs, bronopol (BP) and 2-hydroxymethyl-2-nitro-1,3-propanediol (HNPD), which are β-nitroalcohols (RNAs), was included for comparative purposes.

Chemicals

Diazolidinyl urea (N-Hydroxymethyl-N-(1,3-di(hydroxymethyl)-2,5-dioxoimidazolidin-4-yl)-N'-hydroxymethylurea [DAU]), imidazolidinyl urea (N,N'-methylenebis[N-[3-(hydroxymethyl)-2,5-dioxo-4-imidazolidinyl)]]-urea sodium hydroxymethylglycinate (SMG), 5-Ethyl-3,7-dioxa-1-azabicyclo [3.3.0] octane (7a-Ethyldihydro-1H,3H, 5H-oxazolo[3,4-c]oxazole. [OCT]), 2-bromo-2-nitro-1,3-propanediol or bronopol (BP), hydroxypropyl methyl cellulose (HPMC, 15 centipoise), dextran (high molecular weight=425-575,000 Da), sodium bicarbonate and ethylenediaminetetraacetic acid (EDTA) were obtained from Sigma-Aldrich Corp. (St. Louis, Mo.). DMDM hydantoin was obtained from Oakwood Products, Inc. (West Columbia, S.C.). 2-hydroxymethyl-2-nitro-1-3-propanediol (HNPD) was obtained from TCI Chemicals, Inc. (New York, N.Y.). Riboflavin-5-phosphate was obtained from MP Biomedicals (Santa Ana, Calif.). Dulbecco's phosphate buffered saline (DPBS) solution ($MgCl_2$ & $CaCl_2$ free) was obtained from Life Technologies (Carlsbad, Calif.). All chemical solutions and buffers were prepared fresh using Millipore water (double distilled, de-ionized water, p=18.2 MΩcm at 25° C.) on the day of cross-linking.

Chemical and Riboflavin-Mediated Photochemical Cross-Linking (CXL) of the Cornea Intact cadaveric rabbit heads with clear corneas were obtained fresh (within an hour of sacrifice) in adherence with the ARVO Statement For the Use of Animals in Ophthalmic and Vision Research. FAR solutions at concentrations equivalent to half the maximum allowed value (½max) were administered in a manner designed to simulate therapeutic cross-linking in patients. For all of the corneal experiments (with the notable exception of CXL), the corneal epithelium was left intact. An 8 mm Hessburg-Barron corneal reservoir was affixed to the corneal surface using the supplied syringe vacuum. A single drop of proparacaine (0.5%) was applied to the corneal surface prior to reservoir application. A buffer solution containing 0.1M $NaHCO_3$ at either pH 8.5 or 7.4 was used. The pH of the sample and buffer mixture was titrated to the desired pH just prior to application to the eye using an appropriately concentrated HCl solution. Treatments were conducted over a 30-minute period at 25° C. with refreshing of the solution every five minutes. The control contralateral eye was treated identically with vehicle. Immediately after treatment, a central 6 mm corneal button was trephined from the treated region of each eye, was blotted on both sides using a paper towel to remove excess solution, and was analyzed using differential scanning calorimetry (DSC) [see below]. A minimum of two independent determinations were carried out for each condition described using a fresh cadaver head each time.

As a comparison, the same ex vivo system was used to conduct photochemical cross-linking of rabbit cornea as previously described by Wollensak et al. (Am J Ophthalmol 135:620-627 (2003)) with some changes. To that end, a central 8 mm portion of the corneal epithelium was debrided using a blunt-end scalpel. De-epithelialized corneal tissue was pre-soaked in 0.1% riboflavin-5-phosphate solution in 1.1% HPMC for 5 mins. Thereafter, the cornea was exposed to UV light (λmax=370 nm) at an irradiance of 3 mW/cm$^2$ with an 8 mm aperture for 30 mins using the Optos XLink Corneal Collagen Cross-Linking System (Optos, Dunfermline, UK). Riboflavin solution was refreshed every 3 mins for the course of the treatment. The control contralateral eye was treated identically without irradiation.

Scleral Tissue Cross-Linking

Enucleated porcine globes were purchased from Visiontech, Inc. (Sunnvale, Tex.) and were stored at −80° C. until time of experimentation (1-2 months). Equatorial scleral strips approximately 6 mm×40 mm in size were obtained from multiple eyes. These strips were submerged in DPBS solution containing 1 mM EDTA to inactivate native collagenases and to prevent tissue dehydration during sample preparation. Each strip was further cut into smaller 4 mm×3 mm pieces. The scleral pieces were individually transferred to a 24 well plate and were incubated in 1 ml of cross-linking solution in 0.1M $NaHCO_3$ buffer at either pH 8.5 or 7.4 for 30 mins at 25° C. without refreshing the solution. Four concentrations of FAR solution were tested at each pH: 1) max allowed concentration, 2) ½ max allowed concentration, 3) 1/10 max allowed concentration, and 4) 25 mM. Tissue samples cross-linked with the BNAs BP and HNPD at concentrations of 5 mM (max allowed for BP), 10 mM, and 25 mM were used as positive controls. Negative controls were treated identically with vehicle. Post-treatment, all solutions were aspirated and samples were washed twice using DPBS to remove remnant cross-linking solution before being analyzed by DSC. A minimum of three independent determinations were carried out for each condition using scleral pieces originating from different porcine globes.

Differential Scanning Calorimetry (DSC) and Cross-Link Analysis

Thermal denaturation temperature (Tm) of all samples was measured using a Perkin-Elmer DSC 6000 Autosampler (Waltham, Mass.). Tissue samples were carefully blotted in a standardized, repetitive manner to remove excess solution/DPBS and transferred to pre-weighed 50 ul aluminum pans. The pans were immediately hermetically sealed using a DSC pan sealing press, which is used to prevent tissue dehydration due to evaporative losses. DSC scans were run using Pyris software (version 11.0) from 40° C. to 75° C. at a rate of 1° C./min and denaturation curves representing differential heat flow over time were recorded. DSC heat flow endotherm data was analyzed using the Pyris data analysis peak search function using a calculation limit of ±0.3° C. from the apparent thermal denaturation peak.

Statistical Analysis

T-tests were used to evaluate the significance of observed differences in $T_m$ between cross-linked and control groups. Due to the nature of the ex vivo cadaveric system used for corneal cross-linking, where each cadaver provided the treated eye and contralateral control, corneal samples were subjected to paired t-tests. Conversely, scleral samples were subjected to non-paired t-tests assuming equal variance of data. Significance of all statistical tests was based on an alpha value of 0.05 (p≤0.05). All $\Delta T_s$ values are reported in the form of mean value followed by standard error.

FAR Cytotoxicity Threshold

Healthy human skin fibroblasts (HSFs) from ATCC (Manassas, Va.) were cultured in dermal cell basal media (ATCC) using a serum-free fibroblast growth kit provided by the company (ascorbic acid, EGF/TGF-β1, glutamine, hydrocortisone, insulin and FB growth supplements). Cells were grown in 5% $CO_2$ and 95% ambient air at 37° C. until confluent. Once confluent, the cells were detached and seeded into 24 well plates at a density of 5×10$^4$ cells/well and were once again allowed to reach confluence. Next, cells were treated with FAR solutions over a range of concentrations (0.001 mM-5 mM) for 24 hrs. Following cross-linking exposure, all cell media, including FAR solution, was aspirated and each well was rinsed once with DPBS. Fresh media was then reintroduced and the cells were allowed to recover for 48 hrs. Subsequent to cell recovery, cell toxicity was assessed using a modified version of the trypan blue staining protocol. To that end, all culture media was aspirated and each well was rinsed with DPBS. Next, 0.4% trypan blue solution (Gibco, Grand Island, N.Y., USA) was added to each well for 3 minutes at 25° C. The staining solution was then aspirated and cells were washed twice with DPBS. Finally, extent of trypan blue staining and morphology of cells was visualized using an inverted microscope (Fisher Scientific Cat#12-560-45).

Figure 7:
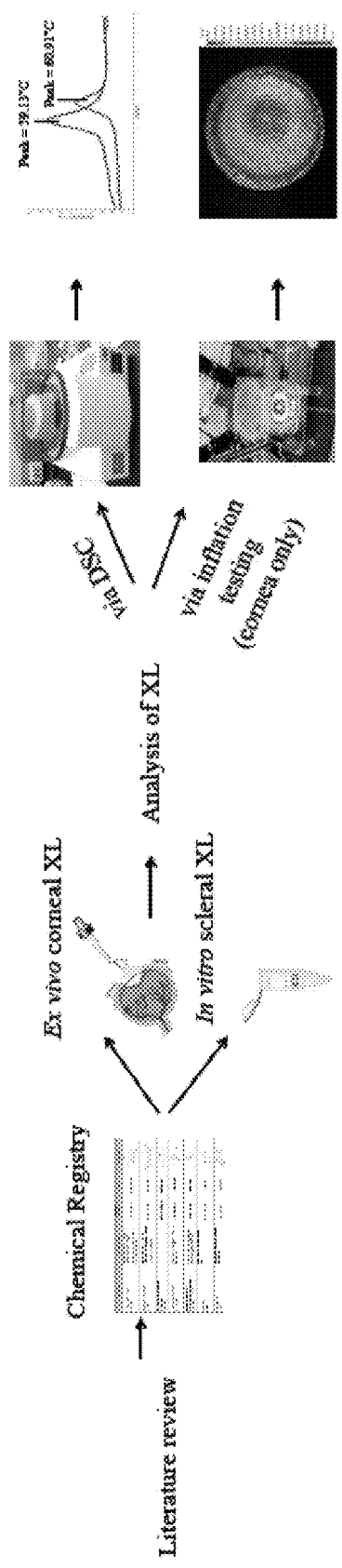

FIG. 7 illustrates a general overview of the disclosed experimental method.

Results

First Experimental Details—Example 1

In a first example of the present invention, N-hydroxymethyl-N-(1,3-di(hydroxymethyl)-2,5-dioxoimidazolidin-4-yl)-N'-hydroxy-methylurea (diazolidinyl urea) was selected and employed in testing. FIG. 1 depicts the net apical displacement response over time for a control cornea and a cornea cross-linked through the use of diazolidinyl urea at pH 8.5. The cross-linked cornea produces a smaller net displacement than the control cornea. The method for inflation chamber testing analysis is described in Myers K M, et al.

Thus, N-hydroxymethyl-N-(1,3-di(hydroxymethyl)-2,5-dioxoimidazolidin-4-yl)-N'-hydroxy-methylurea (diazolidinyl urea) has been shown to be effective for cross-linking at pH 8.5. In comparison to the control, the Tm using diazolidinyl urea (DAU) was shifted 1.92° C.±0.14° C. (n=2). Furthermore, mechanical inflation testing confirmed increased tissue stiffness in pressure ranges mimicking physiological pressure (1.875-45 mmHg). Finally, tissue creep was also diminished under the current loading protocol. See FIG. 1.

First Experimental Details—Example 2

Figure 2:
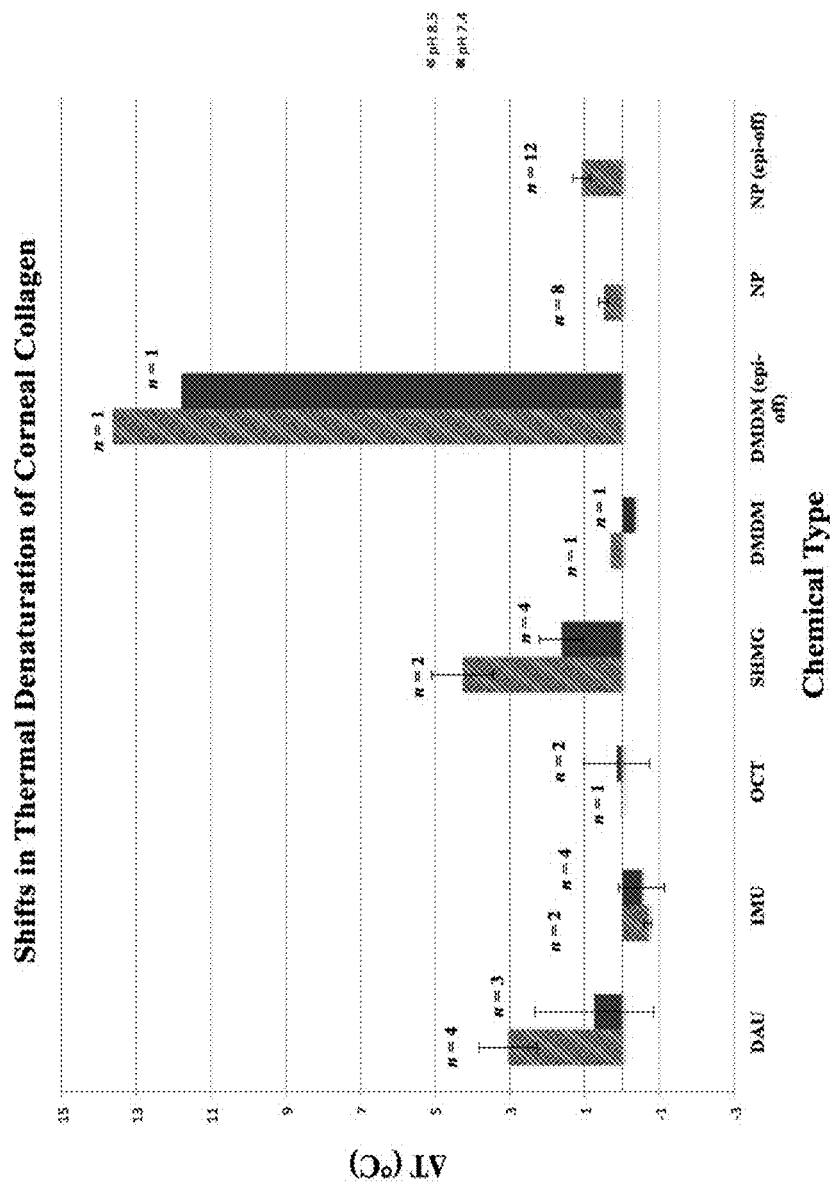
FIG. 2—Cross-linking efficacy of 5 selected formaldehyde releasing agents using the ex vivo rabbit corneal cross-linking simulation setup as compared to a nitroalcohol of 2-nitro-1-propanol (NP).

In a second example of the present invention, several formaldehyde releasing agents were selected and employed in testing. FIG. 2 shows an ex vivo rabbit corneal cross-linking simulation setup used to determine the effects of five selected formaldehyde releasing agents on the thermal stability of collagenous tissue as determined by differential scanning calorimetry (DSC) and measured in upward shifts in thermal denaturation temperature (Tm). The difference in denaturation temperature between treated and paired control ($\Delta T$) represents cross-linking efficacy. The formaldehyde releasing agents tested included N-hydroxymethyl-N-(1,3-di(hydroxymethyl)-2,5-dioxoimidazolidin-4-yl)-N'-hydroxy-methylurea (diazolidinyl urea; labelled DAU), N,N'-methylenebis[N-[3-(hydroxymethyl)-2,5-dioxo-4-imidazolidinyl]]-urea (imidazolidinyl urea; labelled IMU), 5-methyl-1-aza-3,7-dioxabicyclo[3.3.0]octane (labelled OCT), 1,3-dimethylol-5,5-dimethyl-hydantoin (DMDM hydantoin; labelled DMDM), and sodium hydroxymethyl glycinate (labelled SHMG). The cross-linking solution was prepared at half of the maximum allowed concentration (using European regulatory standards) and administered to the right eye for 30 minutes in 0.1 M $NaHCO_3$ at either a pH of approximately 7.4 or approximately 8.5. As a point of comparison, data from an earlier similar experiments in which a nitroalcohol (NA), specifically 2-nitro-1-propanol (labelled NP), was studied is also provided in FIG. 2. The control contralateral eye was treated identically with vehicle. The corneal epithelium was left intact for all samples, unless otherwise noted (see DMDM and NP). The final concentrations were as follows: DAU=9 mM, IMU=7.5 mM, OCT=10.5 mM, SHMG=18.5 mM, DMDM=16 mM, NP 250 mM. In the nitroalcohol (NP) experiments, the cross-linking time was twice (60 minutes) the amount of time used for the selected formaldehyde releasing agents, and the concentration used (250 mM) was significantly higher than the concentration used for these formaldehyde releasing agents. A 50 mM $Na_2HPO_4/NaH_2PO_4$ buffer at pH 8.5 was used for the NP experiments. Even with the longer cross-linking times and higher concentrations, N-hydroxymethyl-N-(1,3-di(hydroxymethyl)-2,5-dioxoimidazolidin-4-yl)-N'-hydroxy-methylurea (diazolidinyl urea), sodium hydroxymethyl glycinate (SHMG), and 1,3-dimethylol-5,5-dimethyl-hydantoin (DMDM hydantoin) are shown to be significantly more effective as cross-linking agents.

First Experimental Details—Example 3

Figure 3:
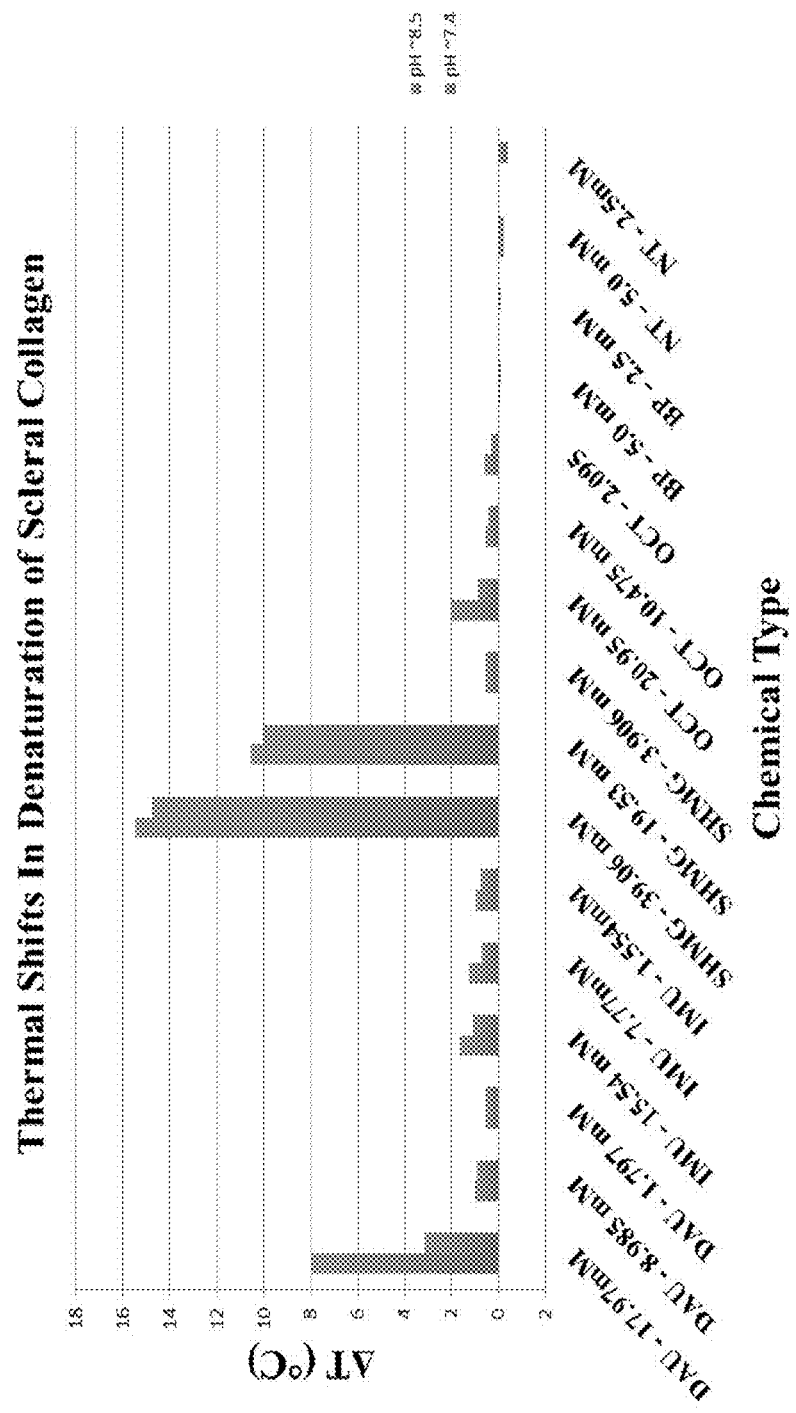
FIG. 3—Cross-linking efficacy of 5 selected formaldehyde releasing agents using the ex vivo rabbit corneal cross-linking simulation setup as compared to nitroalcohols of 2-bromo-2-nitro-1,3-propanediol (BP) and 2-hydroxymethyl-2-nitro-1,3-propanediol (NT).

In a third example of the present invention, several formaldehyde releasing agents were selected and employed in testing. FIG. 3 shows an ex vivo rabbit corneal cross-linking simulation setup used to determine the effects of five selected formaldehyde releasing agents on the thermal stability of collagenous tissue as determined by differential scanning calorimetry (DSC) and measured in upward shifts in thermal denaturation temperature (Tm). The difference in denaturation temperature between treated and paired control ($\Delta T$) represents cross-linking efficacy. The formaldehyde releasing agents tested included N-hydroxymethyl-N-(1,3-di(hydroxymethyl)-2,5-dioxoimidazolidin-4-yl)-W-hydroxy-methylurea (diazolidinyl urea; labelled DAU), N,N'-methylenebis[N-[3-(hydroxymethyl)-2,5-dioxo-4-imidazolidinyl]]-urea (imidazolidinyl urea; labelled IMU), 5-methyl-1-aza-3,7-dioxabicyclo[3.3.0]octane (labelled OCT), 1,3-dimethylol-5,5-dimethyl-hydantoin (DMDM hydantoin; labelled DMDM), and sodium hydroxymethyl glycinate (labelled SHMG). The cross-linking solution was prepared at half of the maximum allowed concentration (using European regulatory standards) and administered to the right eye for 30 minutes in 0.1 M $NaHCO_3$ at either a pH of approximately 7.4 or approximately 8.5. As a point of comparison, comparison runs with two higher order nitroalcohols (NAs) were performed, where the two nitroalcohols were 2-bromo-2-nitro-1,3-propanediol (bronopol; labelled BP) and 2-hydroxymethyl-2-nitro-1,3-propanediol (nitrotriol; labelled NT), as also provided in FIG. 3. The control contralateral eye was treated identically with vehicle. The corneal epithelium was left intact for all samples, unless otherwise noted (see DMDM and NP). The final concentrations were as follows: DAU=9 mM, IMO=7.5 mM, OCT=10.5 mM, SHMG=18.5 mM, DMDM=16 mM, BP=5 mM, NT=5 mM.

Improved Cross-Linking Efficacy Shown for Formaldehyde Releasing Agents (FARs) Versus Nitroalcohols (NAs) Using a Hydrogel Model System Shown in Table 1 below are the results from a parallel study using a hydrogel functionalized amine cross-linking system (polyallylamine, or "PAA") previously published for reactions using nitroalcohols (NAs). Li et al., "Mechanistic and catalytic studies of β-nitroalcohol crosslinking with polyamine," J Appl Polym Sci. 2013; 128:3696-3701. The Table summarizes the results obtained in comparison studies using three of the higher order nitroalcohols previously reported (the nitrotriol HNPD, the nitrodiol MNPD, and the brominated nitrodiol known as Bronopol). The cross-linking efficacy of these nitroalcohol compounds were compared to two of the instantly disclosed formaldehyde releasing agents (diazolidinyl urea (DAU) and imidazolidinyl urea (IMU)). The time to gel formation indicates cross-linking efficacy in this system. In other words, a shorter cross-linking time indicates that the gel formed faster, thus indicating greater cross-linking efficacy. Diazolidinyl urea (DAU) and imidazolidinyl urea (IMU) both exhibited significantly greater cross-linking efficacy over the higher order nitroalcohols (NAs), as indicated by the shorter times to gel formation observed.

TABLE 1

Cross-linking formation with PAA at 37° C. and pH 7.4 phosphate buffered solution

| Chemical cross-linking agent used | 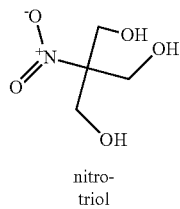 nitro-triol | 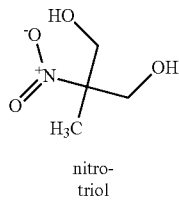 nitro-triol | 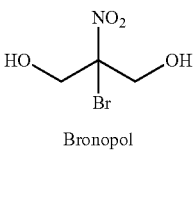 Bronopol |
|---|---|---|---|
| Cross-linking time to gel formation | 29 hr | 66 hr | 42 hr |

| Chemical cross-linking agent used | 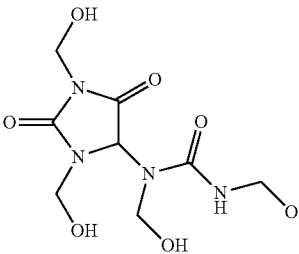 Diazolidinyl Urea | 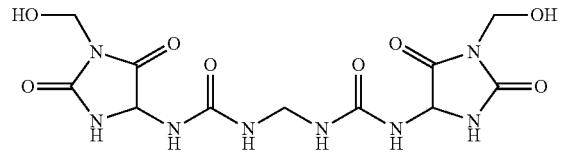 Imidazolidinyl Urea | |
|---|---|---|---|
| Cross-linking time to gel formation | 1.5 hr | 4 hr | |

Furthermore, shown in Table 2 below are experimental results from a study aimed at determining the time and pH dependent release of formaldehyde from these compounds. Shown are the relative amounts of formaldehyde produced by diazolidinyl urea (DAU) versus nitroalcohol (NA) compounds, including 2-hydroxymethyl-2-nitro-1,3-propane-diol (HNPD) (a nitro-triol), 2-methyl-2-nitro-1,3-propane-diol (MNPD) (a nitrodiol), and 2-nitro-1-propanol (NP) (a nitro-monol).

In the study corresponding with Table 2, NMR samples were prepared in NMR tubes as follows: X mg of formaldehyde-releaser, 500 ul of phosphate buffer (pH 7.4), and 500 ul of a solution of acetonitrile in $D_2O$ as internal standard (0.2M). The final concentration of formaldehyde releaser was 1.5 M, and the final concentration of acetonitrile was 0.1 M. The NMR tubes were sealed well and incubated in a water bath at 37° C., and analyzed at the indicated times of 30 and 60 min. A one-dimensional $^{13}$C-NMR spectrum of each solution was recorded on a Bruker NMR instrument at 300 MHz. For each spectrum, the area of the formaldehyde signal at 82.5 ppm was compared with that of the acetonitrile signal at 1.3 ppm (internal standard).

TABLE 2

Quantitative determination of formaldehyde release by $^{13}$C-NMR

| Chemicals | Concentration of formaldehyde (M) [a] | Concentration of formaldehyde (M) [b] |
|---|---|---|
| 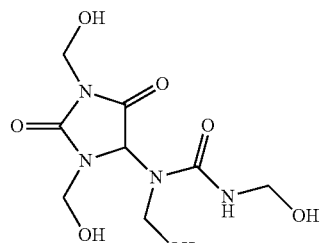 Diazolidinyl urea | 2.044 | 0.319 |

TABLE 2-continued

Quantitative determination of formaldehyde release by $^{13}$C-NMR

| Chemicals | Concentration of formaldehyde (M) [a] | Concentration of formaldehyde (M) [b] |
|---|---|---|
| 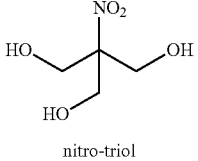 nitro-triol | 0.041 | 0.078 |
| 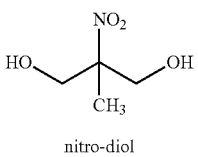 nitro-diol | 0.011 | 0.044 |
| 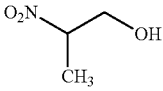 nitro-monol | 0.018 | 0.014 |

Concentration of formaldehyde-releasing agent (FAR), including nitroalcohols is 1.5 M.
[a] Concentration of free formaldehyde (FA): after the sample was incubated in a water bath at 37° C. for 30 min.
[b] Concentration of free formaldehyde (FA): after the sample was incubated in a water bath at 37° C. for 1 hour.

Table 2 indicates that under the conditions studied, diazolidinyl urea (DAU) released approximately fifty (50) times more free formaldehyde (2.044M) than the most potent nitroalcohol (HNPD) (0.041 M) at 30 minutes of incubation time and over four (4) times as much at 60 minutes of incubation time.

Thus, Table 2 shows, for each formaldehyde releaser, the concentration of released formaldehyde after 30 minutes and 1 hour reaction time in phosphate buffered solution (pH=7.4). In this experiment, a prototype compound of a group of formaldehyde releasing agents (FARs), diazolidinyl urea (DAU). The concentration of formaldehyde released from diazolidinyl urea (DAU) within 30 minutes of standing time in alkali buffered solution was determined to be approximately fifty (50) times higher than that of the nitro-triol. In addition, the amount of formaldehyde released from DAU after 1 hour standing time reduced significantly. This could be caused by the reaction of released formaldehyde with breakdown products of the diazolidinyl urea (DAU) starting material. Diazolidinyl urea (DAU) decomposition products have been reported (Lehmann et al., "Characterization and chemistry of imidazolidinyl urea and diazolidinyl urea," *Contact Dermatitis* 2006; 54; 50-8). Similarly, it is to be noted that particularly in the case of 2-nitro-1-propanol (NP), the released formaldehyde can react with the starting material to form the nitrodiol or with 2-nitroethane produced to form the starting material, 2-nitro-1-propanol. This also holds true for the nitrodiol (MNPD) and the nitrotriol (HNPD), both of which can form decomposition products during formaldehyde liberation that could function as a substrate for reaction with the liberated formaldehyde. Finally, it should be pointed out that, in general, the levels of $H_2CO$ released from the three different orders of nitroalcohols (NAs) correspond to the number of potential $H_2CO$ units released from each molecule. That is, the triol can theoretically release three (3) moles $H_2CO$ per parent molecule, the diol can release two (2), and the monol can release one (1).

Second Experimental Details—Example 1

Identification of FARs

From a broad review of the literature, a total of 62 formaldehyde-releasing agents that can potentially be used for corneal and scleral tissue cross-linking were identified. These include FARs commonly found in cosmetics and personal care products as well as those that are used in the textile industry. Table 1 depicts the structures, chemical formulae, toxicity, and other pertinent information of the seven FARs that were chosen for evaluation. None of the chemicals that were tested are known carcinogens. They range in size up to <4000a with IMU being the largest at 388 Da and SMG the smallest at 104 Da [MW=127-23 (Na)=104 Da]. In most but not all cases, mutagenicity data is available, and these chemicals have been found to be non-mutagenic using Ames, micronucleus and other standard assays. Furthermore, they exhibit low organismal toxicity as indicated by high (>1,000 mg/kg,) rat oral $LD_{50}$ values. The exception is BP which has a relatively low $LD_{50}$ Oral, rat=180 mg/kg.

TABLE 1

Characteristics of select FARs pertaining to tissue cross-linking (TXL) in vivo

| Chemical | Structure | Octanol Partition Coefficient (Log P) | % Max Allowed Concentration (mM conversion) | Mutagenicity | Toxicity (method, species, dose, exposure time) |
|---|---|---|---|---|---|
| Diazolidinyl Urea [DAU; CAS No: 78491-02-8; MW: 278.22 g/mol; Formula: C8H14N4O7] | 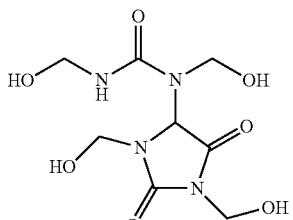 | −5.398 ± 0.866 | 0.5 (17.97 mM) | Non-mutagenic* | $LD_{50}$ Oral-rat-2,600 mg/kg; $LD_{50}$ Dermal-rabbit- >2,000 mg/kg |

TABLE 1-continued

Characteristics of select FARs pertaining to tissue cross-linking (TXL) in vivo

| Chemical | Structure | Octanol Partition Coefficient (Log P) | % Max Allowed Concentration (mM conversion) | Mutagenicity | Toxicity (method, species, dose, exposure time) |
|---|---|---|---|---|---|
| Imidazolidinyl Urea [IMU; CAS No: 39236-46-9; MW: 388.29 g/mol; Formula: C11H16N8O8] | 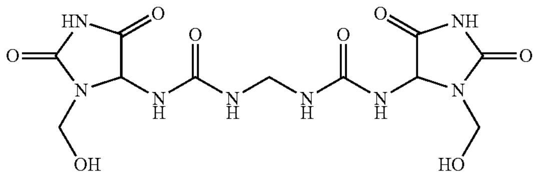 [SMILES: O=C(NCNC(=O)NC1C(=O)NC(=O)N1CO)NC1C(=O)NC(=O)N1CO] | −4.930 ± 0.959 | 0.6 (15.45 mM) | — | LD$_{50}$ Oral-rat-11,300 mg/kg |
| Sodium Hydroxymethyl-glycinate [SMG; CAS No: 70161-44-3; MW: 127.07 g/mol; Formula: C3H6NO3•Na] | 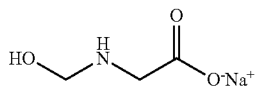 | −1.197 | 0.5 (39.06 mM) | Non-mutagenic† | LD$_{50}$ Oral-rat-2,100 mg/kg, LD$_{50}$ Dermal-rabbit- >2,000 mg/kg |
| DMDM Hydantoin [DMDM; CAS No: 6440-58-0; MW: 188.18 g/mol; Formula C7H12N2O4] | 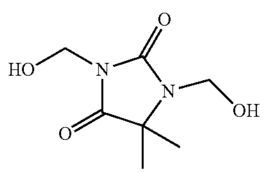 | −1.078 ± 0.654 | 0.6 (31.88 mM) | Non-mutagenic‡ | LD$_{50}$ Oral-rat-3,720 mg/kg; LD$_{50}$ Oral-rat->2,000 mg/kg |
| 5-Ethyl-1-aza-3,7 dioxabicyclo[3.3.0]octane [OCT; CAS No: 7747-35-5; MW: 143.18 g/mol; Formula: C7H13NO2] | 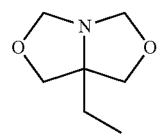 | 0.274 ± 0.496 | 0.3 (20.95 mM) | — | LD$_{50}$ Oral-rat->3,600 mg/kg; LD$_{50}$ Dermal-rabbit-1,948 mg/kg |
| Bronopol [BP; CAS No: 52-51-7; MW: 199.99 g/mol; Formula C3H6BrNO4] | 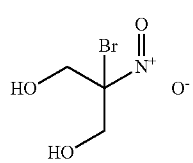 | 1.150 ± 0.631 | 0.1 (5 mM) | Non-mutagenic§ | LD$_{50}$ Oral-rat-180 mg/kg |
| 2-hydroxymethyl-2-nitro-1,3-propanediol [HNPD; CAS No: 126-11-4; MW: 151.12 g/mol; Formula: C4H9NO5] | 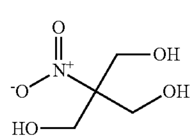 | −0.115 ± 0.770 | — | Non-mutagenic‖ | LD$_{50}$ Oral-rat-1,917 mg/kg; LD$_{50}$ Oral-mouse-10,550 mg/kg |

*non-mutagenic: Ames; Micronucleus Assay
†non-mutagenic: Ames-100% Sodium hydroxymethylglycinate, Mouse Micronucleus; Rat Hepatocyte/DNA Repair Assay; In vivo-In vitro Rat Hepatocyte UDS Assay
‡non-mutagenic Ames-Salmonella-55% DMDM-0.001-5 ul/plate; Salmonella/Mammalian-Microsome Preincubation Mutagenicity Assay-Salmonella-2.0 ul/plate; mutagenic: L5178 TK +/− Mouse Lymphoma Assay; 0.01-1.0 ug/ml; L5178 TK +/− Mouse Lymphoma Assay; 0.006-0.2 ul/ml; Chromosome Aberrations Assay; Chinese Hamster Ovary Cells, 0.3 ul/ml
§non-mutagenic: Ames-Salmonella-with and without metabolic activation-dose not specified
‖non-mutagenic: Ames-Salmonella with and without metabolic activation, 1000 ug/plat Chromosomal Aberration Efficacy of Corneal Cross-Linking The ability of five FARs (DAU, IMU, SMG, DMDM, OCT) to cross-link intact cadaveric rabbit cornea, a substrate for collagenous tissue, was assessed using an ex vivo tissue cross-linking (TXL) simulation set up. Cross-linking effects were measured using differential scanning calorimetry (DSC), an assay method based on changes in thermal denaturation temperature ($T_m$). Results indicate that two out of the seven FARs studied, DAU and SMG, are effective collagen cross-linking agents for the cornea with the epithelium left intact (in the ex vivo simulation setup) at half maximum allowed concentrations. DAU was effective at pH 8.5 and SMG was effective at both pH 8.5 and 7.4. This was evidenced by shifts in the thermal denaturation temperature of corneal tissue, as illustrated in FIG. 4.

Figure 4:
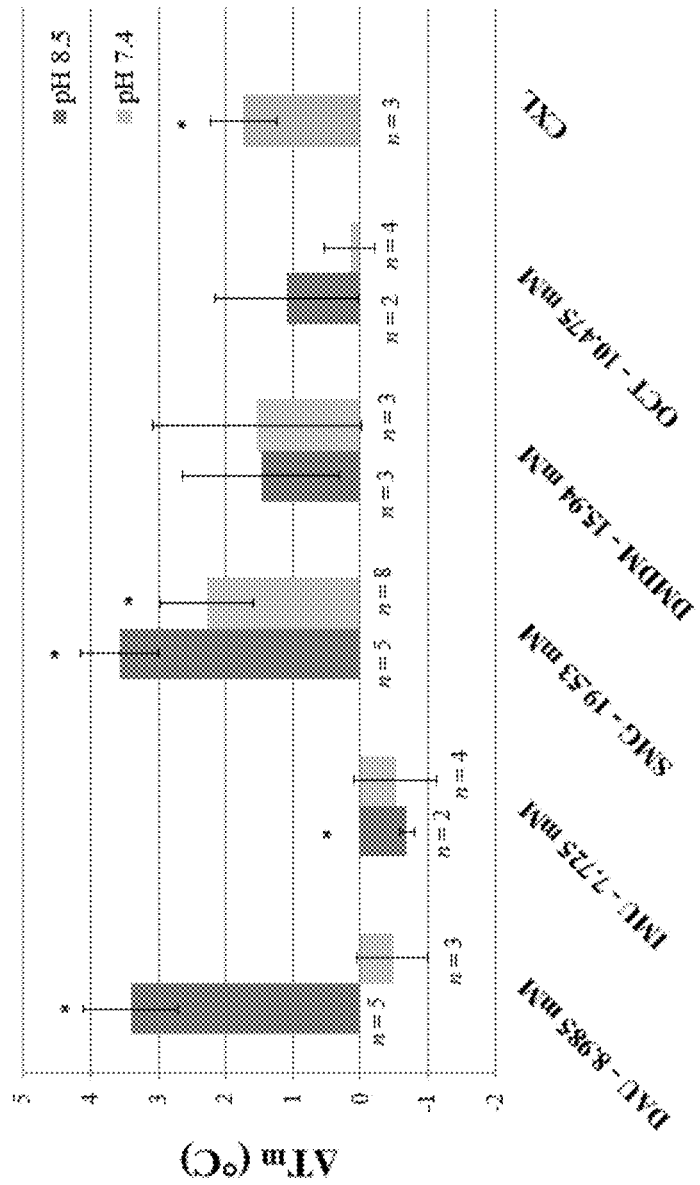
FIG. 4—pH dependent shifts in thermal transition temperatures for 5 formaldehyde releasing agents (FARs) and UVA-riboflavin mediated photochemical cross-linking (CXL) using an ex vivo corneal cross-linking simulation setup FIG. 5—A comparison of pH and concentration dependent shifts in thermal transition temperatures for 5 formaldehyde releasing agents (FARs) using cut porcine scleral pieces FIG. 6—A direct concentration comparison at 25 mM between 5 formaldehyde releasing agents (FARs) and 2 higher order nitroalcohols (HONAs) at two different pH values FIG. 7—An overview of a disclosed experimental method

With respect to FIG. 4, cadaveric rabbit corneas with intact epithelia were cross-linked using the FARs DAU, IMU, SMG, DMDM, and OCT at the indicated concentrations in 0.1M NaHCO$_3$ buffer for 30 mins. Control samples were treated identically with vehicle. A 0.1% riboflavin-5-phosphate solution in 1.1% hydroxypropyl methyl cellulose (HPMC, 15 centipoise) was used for CXL with the corneal epithelium removed. $\Delta T_m$ indicates average shifts in the denaturation temperature of corneal tissue after TXL compared to the controls as measured by DSC. In this case, each experimental determination was paired with the contralateral cornea from the same cadaver head. Dark blue bars depict shifts at pH 8.5 whereas light blue bars depict shifts at pH 7.4. Error bars represent standard error. Asterisks indicate significant changes in $T_m$ following TXL based on paired t-tests on data from at least two independent trials (p≤0.05).

SMG at pH 8.5 showed the greatest upwards shift in $T_m$ ($\Delta T_m$=3.573±0.578° C., p<0.05), followed by DAU at pH 8.5 ($\Delta T_m$=3.398±0.699° C., p<0.05). SMG also showed effective cross-linking at pH 7.4 ($\Delta T_m$=2.281±0.697° C., p<0.05). Some inconsistencies in the shifts in $T_m$ induced by SMG at pH 7.4, however, were noted and a sample size of n=8 was required to reach statistical significance. A negative shift in $T_m$ on the order of ~0.5° C. was observed for DAU at pH 7.4 and for IMU at both pH 8.5 and 7.4, but the shift was only significant for IMU at pH 8.5 ($\Delta T_m$=−0.69±0.697° C., p<0.05). The lack of effect under these conditions may reflect issues related to epithelial permeability since both DAU and IMU are significantly larger than SMG. Furthermore, an increase in $T_m$ was observed for DMDM at both pH 8.5 and 7.4 ($\Delta T_m$=2.04±0.225° C. and 2.13±0.273° C., respectively) and for OCT at pH 8.5 ($\Delta T_m$=1.10±0.246° C.). However, these observed increases in $T_m$ were not statistically significant using paired controls, which included the contralateral eye for each sample. Rabbit cornea cross-linked using UVA-riboflavin (CXL) showed an increase in $T_m$ comparable to values previously reported. In these results, the $\Delta T_m$ following CXL=1.73±0.487° C. The CXL effect is relatively mild from a "thermal transition shifting" standpoint if one considers the potential magnitude of shifts in $T_m$ that may be induced using chemical agents. Lastly, it is worth noting that corneal tissue remained clear to visual inspection using either chemical or photochemical cross-linking treatment.

Efficacy of Scleral Cross-Linking

The results for scleral tissue cross-linking are generally comparable to the results for corneal samples, although different methods of application were used (i.e. refreshing solution every five mins for corneal experiments and not refreshing for scleral experiments). In this case, two additional FARs, BP and HNPD, were also tested. SMG, DAD, and DMDM were found to induce statistically significant cross-linking effects at pH 8.5 and 7.4 (with the exception of SMG at pH 7.4) at concentrations as low as half max allowed. In addition, both a concentration and pH dependent effect was observed for the FARs, as illustrated in FIG. 5.

Figure 5:
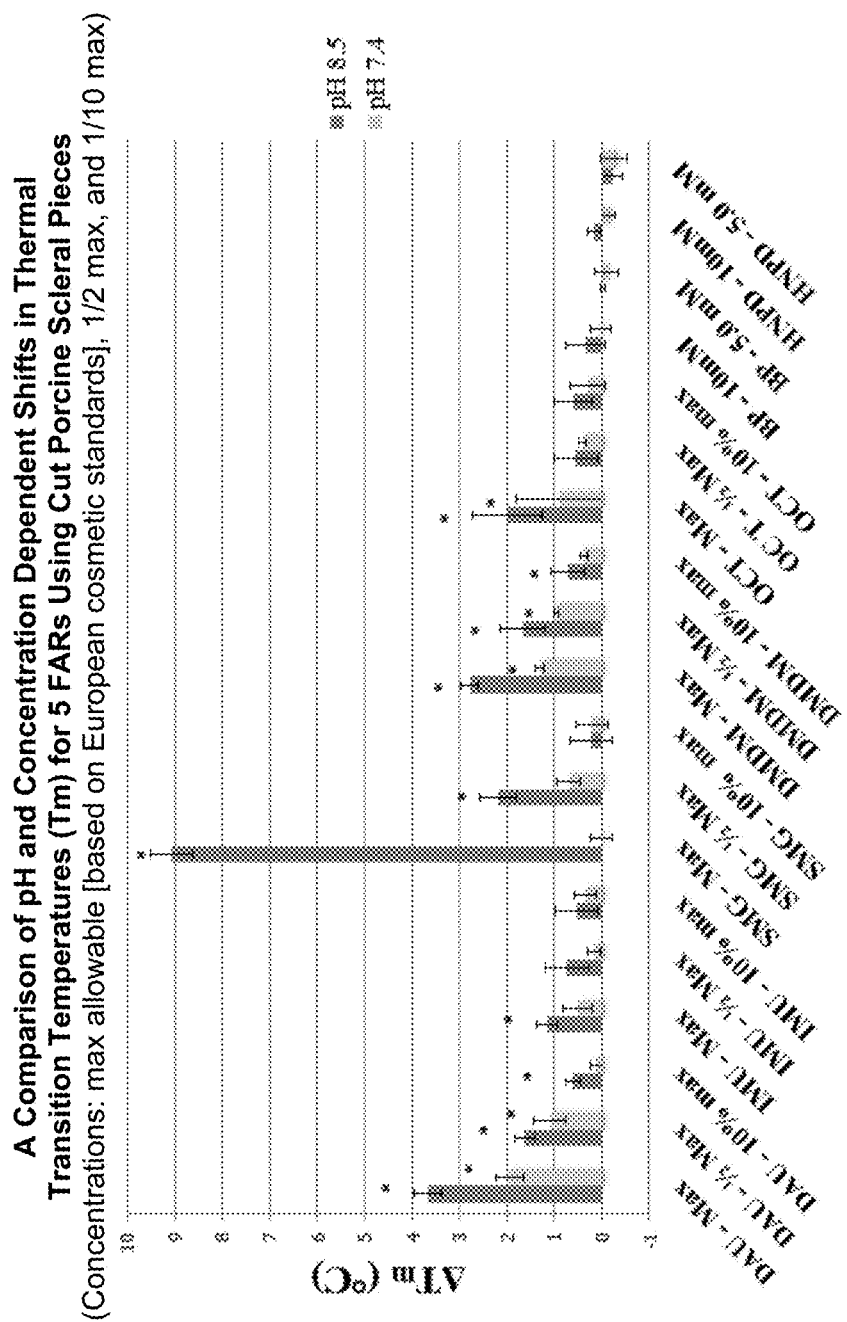

With respect to FIG. 5, porcine scleral tissue was cross-linked using three different concentrations of FAR solution in 0.1M NaHCO$_3$ buffer for 30 mins. Control samples were treated identically with vehicle. $\Delta T_m$ indicates average shifts in the denaturation temperature of scleral tissue after TXL compared to the control as measured by DSC. Dark blue bars depict shifts at pH 8.5 and light blue bars depict shifts at pH 7.4. Error bars represent standard error. Asterisks indicate significant changes in $T_a$ following TXL based on non-paired t-tests on data from three independent trials (p≤0.05).

A notable exception to the concentration dependent effect is seen in the thermal denaturation data for SMG at pH 7.4 and 39.06 mM, where little change in $T_m$ is observed ($\Delta T_n$=0.007±0.222° C., p=0.493), although a dramatic upward shift is seen for the same concentration using a pH of 8.5 ($\Delta T_m$=9.073±0.450° C., p<0.05). The reason for this difference is unclear since, in general, upwards shifts in $T_m$ occur for most FARs, albeit consistently greater for pH 8.5 over 7.4. It should be noted that SMG is highly basic in un-buffered solution, requiring the addition of significant amounts of acid in order to achieve the targeted pH of 7.4. Thus, we speculate that the procedure for titrating the buffered SMG solution to pH 7.4 may have impacted the efficacy of TXL in this case. This phenomenon might also explain the inconsistencies in TXL efficacy experienced when intact cornea was cross-linked using SMG at pH 7.4.

Figure 6:
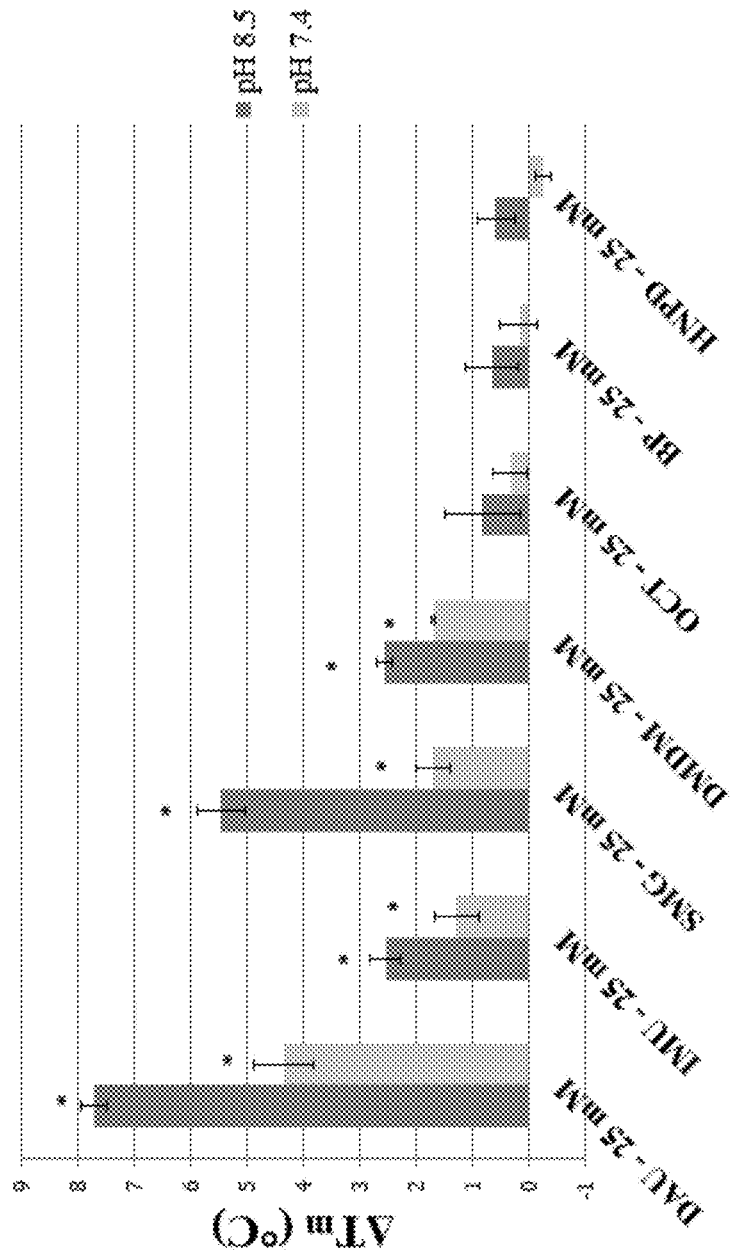

FARs at a concentration of 25 mM were also tested in order to directly compare the cross-linking "potency" of each FAR in comparison to the others, as illustrated in FIG. 6.

With respect to FIG. 6, porcine scleral tissue was cross-linked using FAR solution at 25 mM in 0.1M NaHCO$_3$ buffer for 30 mins. Control samples were treated identically with vehicle. $\Delta T_m$ indicates average shifts in the denaturation temperature of scleral tissue after TXL compared to the control as measured by DSC. Dark blue bars depict shifts at pH 8.5 and light blue bars depict shifts at pH 7.4. Error bars represent standard error. Asterisks indicate significant changes in T following TXL based on non-paired t-tests from data on three independent trials (p≤0.05).

A relatively high concentration was chosen for this comparison for the goal of eliciting a noticeable cross-linking effect using the BNAs HNPD and BP within 30 mins. DAU showed the greatest shifts in thermal denaturation temperature at 25 mM for both pH 8.5 and 7.4 ($\Delta T_m$=7.713±0.226° C. and 4.347±0.538° C., respectively, p<0.05), followed by SMG ($\Delta T_m$=5.463±0.419° C. and 1.697±0.311° C., respectively, p<0.05), DMDM ($\Delta T_m$=2.550±0.142° C. and 1.693±0.033° C., p<0.05), and IMU ($\Delta T_m$=2.543±0.280° C. and 1.280±0.392° C., respectively, p<0.05). OCT, BP, and HNPD exhibited shifts on the order of ~0.5° C. for both pHs (with the exception of HNPD at pH 7.4 which had a negative $\Delta T_m$), but these shifts were not statistically significant, when compared to FIG. 5.

Evaluation of FAR Cytotoxicity

Planar cell culture experiments using Human Skin Fibroblasts (HSFs) were conducted to determine the toxicity thresholds of the FARs. The toxicity threshold was taken to be the highest concentration in mM at which all cells were alive following a 24 hour exposure to the FAR and a 48 hour recovery period. Table 2 shows that, with the exception of BP, the toxicity threshold was found to lie between 0.1 mM and 1 mM fox all FARs. BP was the most toxic to HSFs, with a toxicity threshold between 0.01 mM and 0.001 mM. These values for BP and HNPD were in agreement with those recently reported using the same toxicity testing apparatus (Invest Ophthalmol Vis Sci 55:3247-3257 (2014)).

TABLE 2

FAR toxicity thresholds for human skin fibroblasts

| Concentration (mM) | DAU | IMU | SMG | DMDM | OCT | HNPD | BP |
|---|---|---|---|---|---|---|---|
| 5 | Dead | Dead | Dead | Dead | Dead | Dead | Dead |
| 1 | Dead | Dead | Dead | Dead | Dead | Dead | Dead |
| 0.1 | Alive | Alive | Alive | Alive | Alive | Alive | Dead |
| 0.01 | Alive | Alive | Alive | Alive | Alive | Alive | Dead |
| 0.001 | Alive | Alive | Alive | Alive | Alive | Alive | Alive |
| Control | Alive | Alive | Alive | Alive | Alive | Alive | Alive |

*Human skin fibroblasts (Passage 2) were exposed to FARs for 24 hrs followed by a 48 hr recovery in fresh cell media.

DISCUSSION

Thus, use of formaldehyde releasing agents may find clinical utility as a corneal cross-linking/stiffening agent and could have a significant impact not only on the treatment of keratoconus (which affects younger individuals) but also on post-PRK and post-LASIK keratectasias, which are devastating complications of keratorefractive surgery. These latter mentioned keratectasias are now emerging as a significant long-term complication (5-10 years) of LASIK and PRK surgery of unknown epidemiologic proportions (Binder, et al., 2005). They are also the basis of many of today's PRK- and LASIK-related medical malpractice litigations in ophthalmology and optometry.

The earliest work from Wollensak, Spoerl, and Seiler was reported in 1998. The initial studies were aimed at identifying methods useful for corneal collagen cross-linking and included riboflavin with light exposure, glutaraldehyde, formaldehyde, and other aldehyde sugars. Spoerl, E., et al., "Induction of cross-links in corneal tissue," *Exp. Eye Res.* 1998; 66:97-103; Spoerl, E. and Seiler, T., "Techniques for stiffening the cornea," *J. Refract. Surg.* 1999; 15:711-713. These studies were followed by reports which determined the cytotoxic dose of the treatment on corneal endothelial cells and keratocytes using in vitro cell culture (Wollensak, G., et al., "Corneal endothelial cytotoxicity of riboflavin/UVA treatment in vitro," *Ophthalmic. Res.* 2003; 35:324-328; Wollensak, G., et al., "Keratocyte cytotoxicity of riboflavin/UVA-treatment in vitro," *Eye* 2004; 18:718-722) and the rabbit as a test animal (Wollensak, G., et al., "Endothelial cell damage after riboflavin-ultraviolet-A treatment in the rabbit," *J. Cataract Refract. Surg.* 2003; 29:1786-1790; Wollensak, G., et al., "Collagen fiber diameter in the rabbit cornea after collagen crosslinking by riboflavin/UVA," *Cornea* 2004; 23:503-507). Simultaneously, studies were performed which examined biochemical properties of cross-linked corneal tissue. Basic studies examining thermal denaturation temperature (Spoerl, E., et al., "Thermomechanical behavior of collagen-cross-linked porcine cornea," *Ophthalmologica* 2004; 218:136-140) and resistance to enzymatic digestion (Spoerl, E., et al., "Increased resistance of crosslinked cornea against enzymatic digestion," *Cur. Eye Res.* 2004; 29(1):35-40) indicated that the combination of UVA with riboflavin as a photosensitizer was effective in cross-linking corneal collagen lamellae. These studies were performed in conjunction with biomechanical testing which confirmed increases in Young's modulus (Wollensak, G. and Spoerl, E., "Collagen cross-linking of human and porcine sclera," *J. Cataract Refract. Surg.* 2004; 30:689-95; Kohlhaas, M., et al., "Biomechanical evidence of the distribution of cross-links in corneas treated with riboflavin and ultraviolet A light," *J. Cataract Refract. Surg.* 2006; 32:279-283). Such basic biochemical, biomechanical, and animal studies were then followed by in vivo experiments aimed at determining the potential usefulness of this treatment in the living human eye.

Several chemical cross-linking agents were tested previously by the UVR group in comparison studies with the UVR method and included glucose, ribose, glyceraldehyde, and glutaraldehyde. Of these, only glyceraldehyde and glutaraldehyde, (i.e. aldehydes) were found to produce a significant biomechanical effect (Wollensak, G. and Spoerl, E., 2004). Glutaraldehyde is a well known cross-linking agent used for tissue cross-linking of bioprosthetic heart valves and for tissue fixation prior to viewing by electron microscopy. Its utility as an in vivo cross-linking agent, however, is limited by its significant cytotoxic effects. This is true for several other effective yet toxic aldehyde cross-linking agents, such as formaldehyde and glycoaldehyde. Glyceraldehyde is a physiologic metabolic product, is generally considered non-toxic, and could also be potentially used for topical corneal cross-linking. Another class of cross-linking compounds that could have utility for in vivo cross-linking is the iridoid compounds, of which genipin is an example. Nimni, M. E., "Glutaraldehyde fixation revisited," *Journal of Long-Term Effects of Medical Implants* 2001; 11(3&4):151-161; Jayakrishnan, A. and Jameela, S. R., "Review: Glutaraldehyde as a fixative in bioprostheses and drug delivery matrices," *Biomaterials* 1996; 17:471-484.

This invention uses a formaldehyde releasing agent to cross-link collagen in collagenous tissue.

This invention is an alternative method of tissue cross-linking in the eye, that is, a reaction of collagen with a formaldehyde releasing agent.

This concept has been spurred by recent developments in the treatment of keratoconus. In this case, collagen cross-linking using riboflavin/UVA has been used to stabilize corneal collagen lamellae, preventing the untoward effects of progressive corneal thinning. Thus, this invention involves the application of formaldehyde releasing agent-induced cross-linking to the stiffening of collagen containing tissues for the purpose of stabilization with therapeutic intent. In some cases, collagen cross-linking is desirable as a treatment of certain conditions or to preserve tissue during transplantation as described herein.

Thus, formaldehyde releasing agents, such as diazolidinyl urea (DAU), have been shown to be beneficial corneal cross-linking agents, as indicated by thermal denaturation and biomechanical inflation testing previously discussed.

Moreover, with respect to the second experimental details, both intact cornea and cut scleral tissue pieces were used to test the cross-linking efficacy of compounds known as formaldehyde releasing agents (FARs), comparing the effects against two higher order nitroalcohols (HONAs), BP and HNPD. Three of the FARs were found to be significantly more effective as tissue cross-linking agents when compared to the HONAs, showing both pH and concentration dependent effects. The FARs are a group of compounds commonly used as preservatives in cosmetics and personal care products and as fabric cross-linkers in the textile industry (i.e. for making wrinkle-free clothing), and include bronopol (BP), which is a well-known compound. They are known to release formaldehyde in a pH and concentration dependent manner as determined by $^{13}C$ NMR equilibrium studies, where formaldehyde release amongst FARs popularly used in cosmetics, including DAD, IMU, DMDM, and SMG, was compared.

FARs in commercial use include O- and N-formal compounds. An O-formal group is a formaldehyde entity linked to the rest of the compound via an oxygen atom. An N-formal group is a formaldehyde entity linked to the rest of the compound via a nitrogen atom and can be of two types: amide-based (the nitrogen is a part of an amide) and amine-based (the nitrogen is a part of an amine). The type of group attached to the N-formal group confers different release properties. Slower release occurs with the amide-based N-formals (such as DAU, IMU, and DMDM), which can act as formaldehyde reservoirs, whereas amine based N-formals like SMG have been reported to decompose completely under alkaline conditions and max allowed concentration.

Based on chemical structure alone, DAU would be predicted as the most effective cross-linking agent with the ability to release 4 mols of formaldehyde (contains 4 N-formal groups), followed by HNPD (3 mols), with SMG being the least effective (1 mol). The amount of formaldehyde actually released in solution by each FAR, however, is not as easily predictable as evidenced by the pH and concentration dependent effects noted earlier. The release of formaldehyde is reported to be facilitated at acid pH for SMG, in contrast to the other FARs and nitroalcohols which are facilitated by alkaline pH. Once released from FARs, formaldehyde can react in a number of ways, including reactions with starting material or polymerizing, which can occur under equilibrium conditions. In addition, the availability of reactive substrates under non-equilibrium conditions (such as in the presence of tissue amines from cornea and sclera, for example) can drive the reaction toward formaldehyde release. When used at max allowed concentration (0.5%) as employed herein, formaldehyde release from SMG has been reported to be rapid at pH 8.5, which is consistent with its structure as an amine based N-formal compound.

Chemical tissue cross-linking (TXL) using FARs were compared with riboflavin-mediated photochemical collagen cross-linking (CXL), which is regarded as the "gold standard" of therapeutic corneal cross-linking. Our value for the increase in thermal denaturation temperature following CXL is slightly lower than the shift in the onset of thermal shrinkage ($\Delta T_i$) reported by Spoerl et al. (*Ophthalmologica Journal International d'ophtalmologie International Journal of Ophthalmology Zeitschrift fur Augenheilkunde* 218: 136-140 (2004)) following CXL of the anterior portion of porcine cornea: $\Delta T_n$=1.733±0.487° C. vs. $\Delta T_i$=2.5° C. (originally reported as $\Delta T_i$=5° C. but confirmed to be 2.5° C. (*Invest Ophthalmol Vis Sol* 50:1098-1105 (2009))). A 1.9° C. shift in $T_i$ for porcine cornea cross-linked using the UVA-riboflavin method was previous reported. Therefore, the aforementioned values for $\Delta T_m$ induced by CXL are similar to the shifts in $T_i$ induced by CXL as reported previously even considering the differences in species used (i.e. rabbit vs. porcine cornea).

Corneal epithelial permeability is another consideration that should be borne in mind. These results are favorable since the ex vivo setup simulates conditions that would be encountered in a living system. Of particular interest is the fact that cross-linking effects were induced with the corneal epithelium intact, suggesting that some of these compounds may be able to pass through the epithelial barrier (i.e. SMG MW=127 Da). The ability to induce a cross-linking effect without the need for epithelial removal, if possible, would be a significant advantage over riboflavin-mediated collagen cross-linking (CXL). Differences in transepithelial permeability for IMU, for example, may explain the lack of cross-linking effect seen in the intact cornea, as illustrated in FIG. 4. IMU is the largest of the compounds tested at 388 Da and its size may have hindered passage into the corneal stroma, accounting for the lack of effect in cornea, while positive cross-linking effects were observed for the same compound with cut scleral pieces where permeability was not hindered by an intact corneal epithelium, as illustrated in FIGS. 5 and 6. Molecular size is well-known to affect transcorneal permeability, especially for hydrophilic compounds such as the ones under consideration here.

Regarding thermal denaturation as an assay for tissue cross-linking, several methods have been used previously to evaluate cross-linking changes intentionally induced in collagenous tissues by either chemical or photochemical means and include mechanical testing (either uniaxial strip or inflation testing), enzymatic digestion, gel electrophoresis, and thermal denaturation. Thermal denaturation (as thermal shrinkage temperature) was previously used as an assay measure of chemically and UVA-riboflavin induced cross-linking of collagenous tissue. Tissue cross-linking efficacy was evaluated using an automated instrument that measures change in heat flow over time during the thermal denaturation of a given substance, which is known as differential scanning calorimetry (or DSC). Thermal transition temperature is a concept familiar to the biomaterials industry where it has been used as a means to evaluate the efficacy of tissue cross-linking for decades. DSC produces a denaturation curve, which depicts a major endotherm with the $T_m$ value at its peak. In the case of collagenous tissue, the major endotherm reflects collagen denaturation, which involves triple helical uncoiling and tissue shortening. In addition to collagen cross-linking, it is possible for proteoglycans to be modified in the tissue cross-linking procedure since the core protein contains potential reactive sites. However, this is not expected to alter or contribute to the thermal denaturation of collagen since removal of proteoglycans has been shown not to alter the $T_m$ of collagenous soft tissue.

DSC has been used successfully in many tissue types including tendon, bone, cartilage, and skin, but there are few reports regarding cornea. An additional advantage of DSC is that tissue samples are hermetically sealed, preventing tissue dehydration, which can introduce experimental error into these measurements. Changes that can occur in the water content of tissue are particularly relevant in the case of cornea, which has a large capacity to swell and/or shrink. Finally, the ease of analyzing DSC data using the Pyris software adds to the effectiveness of using DSC for cross-link analysis.

In order to directly assess the toxicity of these chemicals, an in vitro cell toxicity experiment was conducted using human skin fibroblasts (HSFs) and these FARs. The toxicity threshold of all FARs tested was determined to be below 1 mM with the exception of bronopol, which was the most toxic (toxicity threshold below 0.01 mM). Past cell toxicity studies using HSFs indicated that genipin and glutaraldehyde both have toxic thresholds on par with bronopol. Glyceraldehyde was previously shown to be the least toxic cross-linking agent for HSFs, with a toxic threshold of 1 mM. Therefore, the toxicity of FARs lies between the toxicity of glutaraldehyde and glyceraldehyde, with glyceraldehyde being the least toxic. The cell toxicity thresholds determined are not designed to provide direct clinical information regarding potentially applicable concentrations, but rather, as a means to compare toxicity between compounds.

Finally, with regards to safety, owing to their widespread use in cosmetics and by the textile industry, where workplace hazards are closely scrutinized, the FARs have been extensively tested in European safety studies by the Scientific Committee on Cosmetics and Non-food Products following the commission of Cosmetic Products Directive 76/768/EC by the Council of the European Communities in 1976. The result of the Cosmetic Directive was a delineation of which FARs can appear in cosmetics and personal care products and at what concentrations. The maximum allowed concentrations of FARs as defined in the Cosmetic Directive were adapted on the belief that working within the maximum allowed value would be a good starting point in evaluating effects that could be induced in patients.

In conclusion, the aforementioned disclosure has demonstrated a novel therapeutic application for formaldehyde releasing agents commonly employed in consumer personal care products. Two of these agents, DAU and SMG, have shown effective cross-linking abilities in intact cornea and cut scleral pieces as indicated by shifts in thermal denaturation temperature (T). In light of the current growing therapeutic cross-linking application in both the cornea and sclera, FARs may have therapeutic potential in the treatment of diseases such as keratoconus and myopia. Continued screening of FARs from the compiled registry could lead to the identification of additional potent cross-linking agents.

Additional references relating to this invention include the following: Abraham, V. C., et al., "High content screening applied to large-scale cell biology," Trends in Biotechnology 2004; 22(1):15-22; Amano, S., et al., "Comparison of central corneal thickness measurements by rotating scheimpflug camera, ultrasonic pachymetry, and scanning-slit corneal topography," Ophthalmology 2006; 113:937-941; Bailey, A. J., "Molecular mechanisms of ageing in connective tissues," Mech. Aging Dev. 2001; 122:735-55; Banse, X., et al., "Cross-link profile of bone collagen correlates with structural organization of trabeculae," Bone 2002; 31(1):70-76; Bednarz, J., et al., "Effect of three different media on serum free culture of donor corneas and isolated human corneal endothelial cells," Br. J. Ophthalmol. 2001; 85:1416-1420; Brady, J. D. and Robins, S. P., "Structural characterization of pyrrolic cross-links in collagen using a biotinylated Ehrlich's reagent," J. Biol. Chem. 2001; 276(22):18812-18818; Chiou, A. G. Y., et al., "Clinical corneal confocal microscopy," Survey of Ophthalmology 2006; 51(5):482-500; Eyre, D. R., et al., "Cross-linking in collagen and elastin," Ann. Rev. Biochem. 1984; 53:717-746; Lackner, B., et al., "Repeatability and reproducibility of central corneal thickness measurement with pentacam, orbscan, and ultrasound," Optometry and Vision Science 2005; 82:892-899; Lee, M. Y. and Dordick, J. S., "High-throughput human metabolism and toxicity analysis," Current Opinion in Biotechnology 2006; 17:619-627; McLaren, J. W., et al., "Corneal thickness measurement of confocal microscopy, ultrasound, and scanning slit methods," Am. J. Ophthalmol. 2004; 137:1011-1020; Naor, J., et al., "Corneal endothelial cytotoxicity of diluted providone-iodine," J. Cataract Refract. Surg. 2001; 27:941-947; Sady, C., et al., "Advanced Maillard reaction and crosslinking of corneal collagen in diabetes," Biochem. Biophys. Res. Com. 1995; 214(3):793-797; Sell, D. R. and Monnier, V. M., "Structure elucidation of a senescence cross-link from human extracellular matrix," J. Biol. Chem. 1989; 264(36):21597-21602; Skinner, S. J. M., "Rapid method for the purification of the elastin cross-links, desmosine and isodesmosine," J. Chromatog. 1982; 229:200-204; Wollensak, G., et al., "Stress-strain measurements of human and porcine corneas after riboflavin-ultraviolet-A-induced cross-linking," J. Cataract Refract. Surg. 2003; 29:1780-1785.

What is claimed is:

1. A composition for ophthalmic administration comprising a formaldehyde releasing agent, sodium bicarbonate, and an ophthalmically suitable carrier or excipient, wherein the formaldehyde releasing agent is 1-(phenylmethoxy)-methanol, N-hydroxymethyl-N-(1,3-di(hydroxymethyl)-2,5-dioxoimidazolidin-4-yl)-N'-hydroxy-methylurea, 1,3-dimethylol-5,5-dimethyl-hydantoin, N,N'-methylenebis[N-[3-(hydroxymethyl)-2,5-dioxo-4-imidazolidinyl]]-urea, sodium hydroxymethyl glycinate, 5-bromo-5-nitro-1,3-dioxane, 3,5,7-triaza-1-azoniatricyclo[3.3.1.13,7]decane, 1(3-chloro-2-propen-1-yl)-chloride(1:1), 4,5-dihydroxy-1,3-dimethyl-2-Imidazolidinone, 4,5-dihydroxy-1,3-bis(hydroxymethyl)-2-Imidazolidinone, tetrahydro-1,3-bis(hydroxymethyl)-2(1H)-pyrimidinone, tetrahydro-1,3,4,6-tetrakis(hydroxymethyl)-imidazo[4,5-d]imidazole-2,5(1H, 3H)-dione, polyoxymethylene urea, 4,4-dimethyloxazolidine, 7a-ethyldihydro-1H,3H,5H-oxazolo[3,4-c]oxazole, 4,5-dihydroxy-1,3-bis(hydroxymethyl)-2-imidazolidinone methylated, dimethylhydantoin formaldehyde resin, 4,5-dihydroxy-1,3-bis(hydroxymethyl)-2-imidazolidinone, 1,3-bis(hydroxymethyl)-2-imidazolidinone, N,N'-bis(hydroxymethyl)-urea, 1,3-ethyleneurea, (Z)-3-(bis(2-hydroxyethyl)amino)-2-(2-hydroxyethyl(hydroxymethyl)amino) prop-2-en-1-ol, 1,3,5-trietethyl-1,3,5-tiazinane, 4,5-dihydroxy-2-imidazolidinone, 1-(hydroxymethyl)-5,5-dimethyl-2,4-Imidazolidinedione, 1,3,5,7-tetraazatricyclo[3.3.1.13,7]decane, 4,4'-methylenebis-morpholine, 2-chloro-N-(hydroxymethyl)-acetamide, N-(hydroxymethyl)-urea, polyoxymethylene melamine, 1,1'-[methylenebis(oxymethylene)]bis-benzene, 1,6-dihydroxy-2-5-dioxahexane (1,1'-[1,2-ethanediylbis(oxy)]bis-methanol, 2,4-imidazolidinedione, hydroxymethyl-5-5-dimethyl-2-4-imidazolidinedione, 3-hydroxymethyl-5-5-dimethylimidazolidine-2,4-dione, dimethoxy-methane, N-methylolethanolamine, 1H,3H,5H-oxazolo[3,4-c]oxazole-7a(7H)-methanol, Bioban N-95 (mixture of 5-methyl-1-aza-3,7-dioxabicyclo[3.3.0]octane, 5-hydroxymethoxymethyl-1-aZa-3,7-diox abicyclo[3.3.0]octane, and higher hydroxyalkoxymethyl oligomers), 5-methyl-1-aza-3,7-dioxabicyclo[3.3.0]octane, 4,4-dimethyl-oxazolidine, 4-ethyl-2-(1-methylethyl)-oxazolidine, diethylamine/2-methyl-2 nitro-1,3-propanediol, dimethylamine-2-methyl-2-nitro-1,3-propanediol, pyrrolidine/2-methyl 2-nitro-1,3-propanediol, 2-furfural/2-methyl 2-nitro-1,3-propanol, N-hydroxy-2-propanamine, N-hydroxy-1-propanamine, N-hydroxy-ethanamine, N-hydroxy-2-methyl-2-propanamine, N-hydroxy-cyclohexanamine, N-ethyl-N-hydroxy-ethanamine, 1,1'-[methylenebis(oxy)]bis[2-methyl-2-nitro-(9CI)]-propane, hydroxylamine (HA) nitrone, N-ethylhydroxylamine (EHA) nitrone, N-propylhydroxylamine (PHA) nitrone, N-t-butyl hydroxylamine (tBuHA) nitrone, Cyclohexanedicarboxaldehyde (CHDA)-bis-isopropylhydroxylamine (IPHA) nitrone, N-benzyl hydroxylamine (N-BzHA) nitrone, or vanillin-isopropylhydroxylamine (IPHA) nitrone.

2. A composition for ophthalmic administration comprising a formaldehyde releasing agent, sodium bicarbonate, and an ophthalmically suitable carrier or excipient, wherein the formaldehyde releasing agent is 1-(phenylmethoxy)-methanol, N-hydroxymethyl-N-(1,3-di(hydroxymethyl)-2,5-dioxoimidazolidin-4-yl)-N'-hydroxy-methylurea, 1,3-dimethylo-5,5-dimethyl-hydantoin, N,N'-methylenebis[N-[3-(hydroxymethyl)-2,5-dioxo-4-imidazolidinyl]]-urea, sodium hydroxymethyl glycinate, or 5-methyl-1-aza-3,7-dioxabicyclo[3.3.0]octane.

3. The composition of claim 2 wherein the formaldehyde releasing agent is N-hydroxymethyl-N-(1,3-di(hydroxymethyl)-2,5-dioxoimidazolidin-4-yl)-N'-hydroxy-methylurea.

4. The composition of claim 1 wherein the formaldehyde releasing agent is in an aqueous solution having a pH effective for cross-linking.

5. The composition of claim 4 wherein the pH is 7.4.

6. The composition of claim 4 wherein the pH is 8.5.

7. The composition of claim 2 wherein the formaldehyde releasing agent is in an aqueous solution having a pH effective for cross-linking.

8. The composition of claim 3 wherein the formaldehyde releasing agent is in an aqueous solution having a pH effective for cross-linking.

9. The composition of claim 7 wherein the pH is 7.4.
10. The composition of claim 7 wherein the pH is 8.5.
11. The composition of claim 8 wherein the pH is 7.4.
12. The composition of claim 8 wherein the pH is 8.5.

* * * * *